(12) United States Patent
Schrattenholz

(10) Patent No.: US 8,466,144 B2
(45) Date of Patent: Jun. 18, 2013

(54) MUSCARINIC ANTAGONISTS WITH PARP AND SIR MODULATING ACTIVITY AS CYTOPROTECTIVE AGENTS

(75) Inventor: André Schrattenholz, Mainz (DE)

(73) Assignee: Proteosys AG, Mainz (DE)

( * ) Notice: Subject to any disclaimer, the term of this patent is extended or adjusted under 35 U.S.C. 154(b) by 1441 days.

(21) Appl. No.: 11/632,649

(22) PCT Filed: Jul. 18, 2005

(86) PCT No.: PCT/EP2005/007804
§ 371 (c)(1),
(2), (4) Date: Apr. 9, 2007

(87) PCT Pub. No.: WO2006/008118
PCT Pub. Date: Jan. 26, 2006

(65) Prior Publication Data
US 2007/0265251 A1 Nov. 15, 2007

Related U.S. Application Data

(60) Provisional application No. 60/588,354, filed on Jul. 16, 2004, provisional application No. 60/620,323, filed on Oct. 21, 2004, provisional application No. 60/656,378, filed on Feb. 28, 2005, provisional application No. 60/656,379, filed on Feb. 28, 2005.

(51) Int. Cl.
*A61K 31/551* (2006.01)
*A61P 25/00* (2006.01)

(52) U.S. Cl.
USPC . 514/220; 514/630; 514/211.08; 514/211.09; 514/211.15

(58) Field of Classification Search
USPC ........... 514/211, 220, 211.08, 211.09, 211.15
See application file for complete search history.

(56) References Cited

U.S. PATENT DOCUMENTS

| | | | |
|---|---|---|---|
| 6,455,552 B1 * | 9/2002 | Dawson | 514/356 |
| 2002/0142303 A1 | 10/2002 | Parekh et al. | |
| 2004/0137069 A1 * | 7/2004 | Takruri | 424/488 |

FOREIGN PATENT DOCUMENTS

| | | |
|---|---|---|
| EP | 0309422 A2 | 3/1989 |
| GB | 2 239 396 A | 7/1991 |
| WO | WO 02/096418 A | 12/2002 |

OTHER PUBLICATIONS

Mabley, "Anti-inflammatory effects of a novel, potent inhibitor of poly(ADP-ribose) polymerase", Inflammation Research, 2001, 50, pp. 561-569.*
Nikolov R., "Alzheimers disease therapy—An update", Drug News and Perspectives, vol. 11, No. 4, May 1998, pp. 248-255.
Database Biosis 'Online!, Pompilio et al., "Comparative Evaluations on Short-Term Treatment with Cimetidine and Pirenzepine in Duodenal Ulcer and in Acute Inflammatory Pathology of the Stomach and Duodenum", Database accession No. PREV198375090208 abstract & Rassegna Di Medicina Sperimentale, vol. 28, No. 9, 1981, pp. 567-574.
Database Embase 'Online!, Londong W., "Present status and future perspectives of muscarinic receptor antagonists", Database accession No. EMB-1987043228 abstract & Scandinavian Journal of Gastroenterology, Supplement, 1986 Norway, vol. 21, No. Suppl. 125, 1986, pp. 55-60.
Cruickshang et al., "Involvement of M1 muscarinic receptors in the initiation of cholinergically induced epileptic seizures in the rat brain", Brain Research, vol. 643, No. 1-2, 1994, pp. 125-129.
Packard et al., "Post-Training Injection of the Acetylcholine M-2 Receptor Antagonist AF-DX-116 Improves Memory", Brain Research, vol. 524, No. 1, 1990, pp. 72-76.
Li Le et al., "Research Progress on Selective Muscarinic-like Choline Receptor Agonists and Antagonists", World Pharmacy-Synthetic Biochemical, Preparation Section, vol. 18, No. 1, pp. 8-13, Feb. 15, 1997.
An English translation of an Office Action issued for the parallel Chinese Application No. 200580027833.6, dated Apr. 3, 2009, 3 pgs.
Felder et al., "Therapeutic Opportunities for Muscarinic Receptors in the Central Nervous System", Journal of Medicinal Chemistry, vol. 43, No. 23, Nov. 16, 2000. pp. 4333-4353.

* cited by examiner

*Primary Examiner* — Sreeni Padmanabhan
*Assistant Examiner* — Sahar Javanmard
(74) *Attorney, Agent, or Firm* — Rothwell, Figg, Ernst & Manbeck, P.C.

(57) ABSTRACT

The present invention relates to generally to the cytoprotective activity of mixed muscarinic inhibition/PARP modulation and in particular to the use of dual inhibitors of M1 muscarinic receptor and poly(ADP-ribose) polymerase (PARP) as neuroprotective medicaments, particularly as medicaments for the prevention and/or treatment of neurological diseases. Particularly preferred compounds are condensed diazepinones, e.g. condensed benzodiazepinones such as pirenzepine or compounds which are metabolized to condensed benzodiazepinones such as olanzapine.

7 Claims, 16 Drawing Sheets

Figure 2

Figure 1:
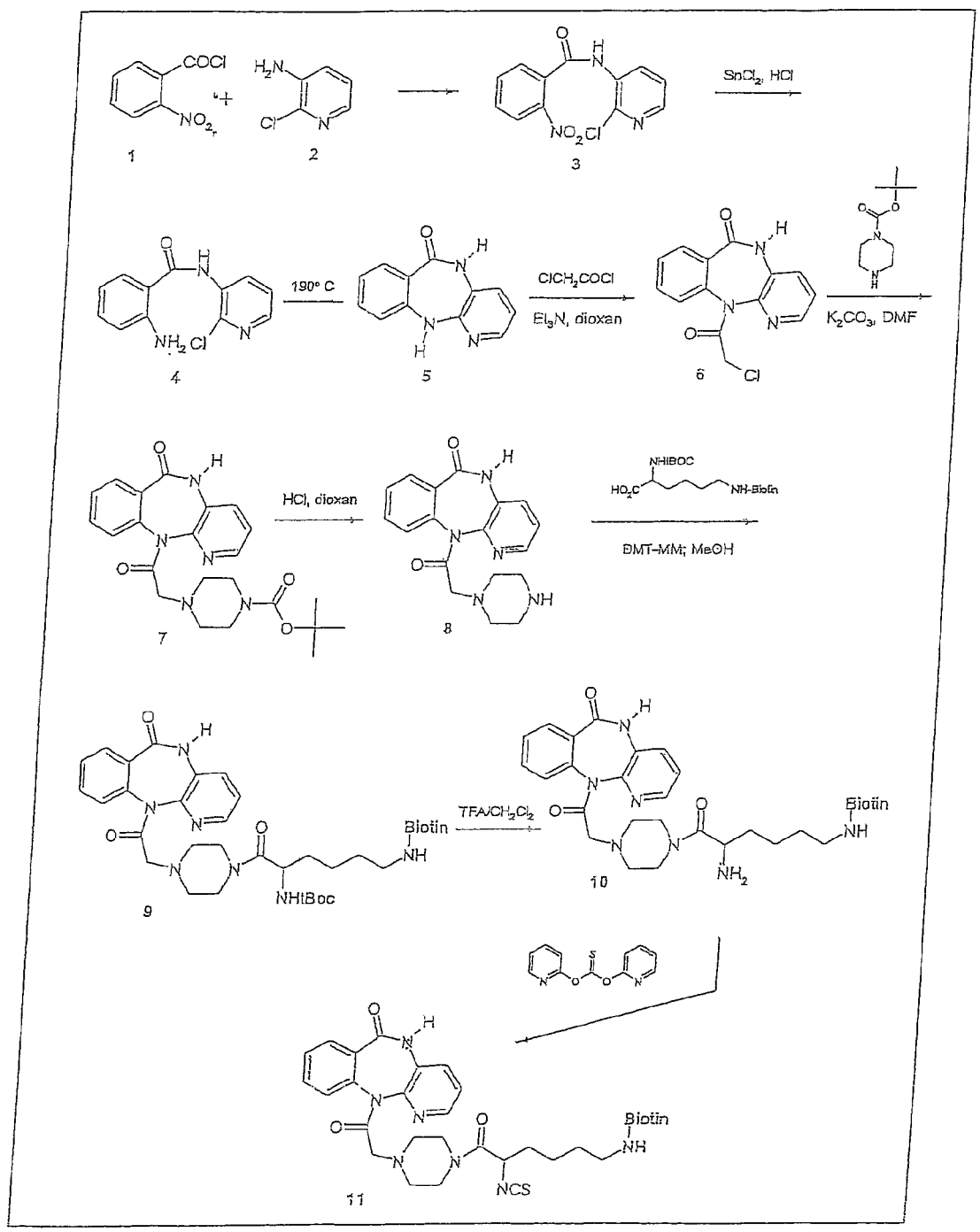

| 2a | |
|---|---|
| Pirenzepine | LS 75 |

| 2c | Chemical ischemia, 1-45 min, 3 mM KCN, glucose deprivation | |
|---|---|---|
| 1 µM LS-75 (PBD) | + | − |
| (min) | 1  2  5  10  30  45 | 1  2  5  10  30  45 |
| Cox-2 (68 & 69 kD) | | |
| β-Actin (41 kD) | | |
| iNOS (131 kD) | | |
| PARP-1 (113 & 89 kD) | 113  89 | 113  89 |

| 2f (µM) | $EC_{50}$ Excitotoxic paradigm (NMDA, HCA) | $EC_{50}$ ß-amyloid toxicity (10 µM Aß 1-40) | $EC_{50}$ Chemical ischemia (45 min, 3 mM KCN) |
|---|---|---|---|
| LS 75 | 1 | 0.1 | 0.3 |
| Pirenzepine | 2 | 0.1 | 0.5 |

|  | # of cells 1. stimulation | # of cells 2. stimulation after ischemia | Surviving cells [%] |
|---|---|---|---|
| Control | 376 | 20 | 5,3 ± 1,6 |
| LS 75 (1µM) | 294 | 218 | 74,15 ± 3,6 |
| Pirenzepine (1µM) | 350 | 235 | 67,1 ± 5,6 |

| | # of cells 1. stimulation | # of cells 2. Stimulation after ß-A | Surviving cells [%] |
|---|---|---|---|
| ß-amyloid1-40 | 220 | 22 | 10.0 ± 2.9 |
| ß-amyloid1-40 + LS 75 (1 µM) | 274 | 244 | 89.1 ± 2.7 |

MUSCARINIC ANTAGONISTS WITH PARP AND SIR MODULATING ACTIVITY AS CYTOPROTECTIVE AGENTS

CROSS REFERENCE TO RELATED APPLICATION

This application is a 35 USC §371 National Phase Entry Application from PCT/EP2005/007804, filed Jul. 18, 2005, and designating the United States, which claims the benefit of U.S. Provisional Applications 60/588,354 filed Jul. 16, 2004, 60/620,323 filed Oct. 21, 2004, 60/656,378 filed Feb. 28, 2005, and 60/656,379 filed Feb. 28, 2005.

DESCRIPTION

The present invention relates to generally to the cytoprotective activity of mixed muscarinic inhibition/PARP modulation and/or SIR2 modulation and in particular to the use of dual inhibitors of M1 muscarinic receptor and poly (ADP-ribose) polymerase (PARP) and/or modulators of SIR2 as neuroprotective medicaments, particularly as medicaments for theprevention and/or treatment of neurological diseases. Particularly preferred compounds are condensed diazepinones, e.g. condensed benzodiazepinones such as pirenzepine or compounds which are metabolized to condensed benzodiazepinones such as olanzapine.

Pirenzepine (5,11-dihydro-11[(4-methyl-1-piperazinyl)-acetylJ-6H-pyrido-[2,3-b]-[1,4]benzodiazepine-6-one), is a topical antiulcerative M1 muscarinic antagonist, that inhibits gastric secretion at lower doses than are required to affect gastrointestinal motility, salivary, central nervous system, cardiovascular, ocular, and urinary function. It promotes the healing of duodenal ulcers and due to its cytoprotective action is beneficial in the prevention of duodenal ulcer recurrence. It also potentiates the effect of other antiulcer agents such as cimetidine and ranitidine. It is generally well tolerated by patients. The M1 muscarinic effect of pirenzepine is thought to be an explanation for this and a variety of additional effects in other indications, listed below.

For the preparation, pharmacology, pharmacokinetics and mechanism of action of pirenzepine, the following references are referred to:
Preparation: FR. Patent. 1,505,795 (1967 to Thomae), CA. 70, 4154w (1969).
Pharmacology: W. Ebenem et al *Arzneimittel-Forsch.* 27, 356 (1977).
Pharmacokinetics: R. Hammes et al., *ibid.* 928.
Mechanism of action: G. Heller et al, *Verh. Deut Ges. Inn. Med.* 84, 991 (1978), C.A. 90, 132984s (1979).
Human pharmacology: H. Brunnen et al., *Arzneimittel-Forsch.* 27, 684 (1977). Multicenter controlled clinical trial: *Scand. J. Gastroenterol.* 17, Suppl. 81, 1-42 (1982).
Review of pharmacology and therapeutic efficacy: A.
A. Carmine, R. N. Brogden, *Drugs* 30, 85-126 (1985).
Comprehensive description: H. A. El-Obeid et al., in *Analytical Profiles of Drug Substances*, Vol 16, K. Florey, Ed. (Academic Press, New York, 1987) pp 445-506.

The M1 muscarinic effect of pirenzepine is thought to responsible for vago-mimetic neuro-humoral regulation potentially useful for treatment of chronic heart failure patients and of patients recovering from myocardial infarction or generally in hypertension [Jakubetz J Human cardiac beta1- or beta2-adrenergic receptor stimulation and the negative chronotropic effect of low-dose pirenzepine. Clin Pharmacol Ther—2000 May; 67(5): 549-57. Hayano T, Shimizu A, Ikeda Y, Yamamoto T, Yamagata T, Ueyama T, Furutani Y, Matsuzaki M Paradoxical effects of pirenzepine on parasympathetic activity in chronic heart failure and control.lnt. J. Cardiol. 1999 January;68(1):47-56. Pedretti R F, Colombo E, Braga S S, Ballardini L, Caru B Effects of oral pirenzepine on heart rate variability and baroreceptor reflex sensitivity after acute myocardial infarction. J. Am. Coll. Cardiol. 1995 Mar. 15;25(4):915-21. Wilhelmy R, Pitschner H, Neuzner J, Dursch M, Konig S Selective and unselective blockade of sympathicus and parasympathicus and vagal enhancement by pirenzepine: effects on heart rate and heart rate variability in healthy subjects. Clin Sci (Colch)1996; 91 Suppl: 124.].

Pirenzepine has also been implicated in some CNS-related diseases based on its M1 muscarinic inhibitory action, e.g. it is used as a co-medication to antipsychotic drugs (Hedges D, Jeppson K, Whitehead P Antipsychotic medication and seizures: a review. Drugs Today (Barc). 2003 July;39(7):551-7; Schneider B, Weigmann H, Hiemke C, Weber B, Fritze J.Reduction of clozapine-induced hypersalivation by pirenzepine is safe. Pharmacopsychiatry. 2004 March; 37(2):43-5). A potential role of muscarinic receptors in schizophrenia is assumed to be the underlying reason (Katerina Z, Andrew K, Filomena M, Xu-Feng H. Investigation of m1/m4 muscarinic receptors in the anterior cingulate cortex in schizophrenia, bipolar disorder, and major depression disorder. Neuropsychopharmacology. 2004 March;29(3): 619-25). Also selective muscarinic M1 agonists have been implicated in the release and processing of amyloid precursor protein potentially relevant in Alzheimer's disease (Qiu Y, Wu X J, Chen H Z. Simultaneous changes in secretory amyloid precursor protein and beta-amyloid peptide release from rat hippocampus by activation of muscarinic receptors. Neurosci Lett. 2003 November 27;352(1):41-4; Qiu Y, Chen H Z, Wu X J, Jin Z J.6beta-acetoxy nortropane regulated processing of amyloid precursor protein in CHOM1 cells and rat brain. Eur J Pharmacol. 2003 May 2;468(1):1-8.).

Pirenzepine is used together with drugs like olanzapine or clozapine to suppress side effects (e.g. emesis or hypersalivation) in cancer or schizophrenia treatments (Bai Y M, Lin C C, Chen J Y, Liu W C. Therapeutic effect of pirenzepine for clozapine-induced hypersalivation: a randomized, double-blind, placebo-controlled, cross-over study. J Clin Psychopharmacol. 2001 December;21(6):608-11).

Pirenzepine has also been found to be effective in the reduction of progression of myopia, especially in children with promising efficacy results and acceptable safety profile (Gilmartin B. Myopia: precedents for research in the twenty-first century. Clin Experiment Ophthalmol. 2004 June;32(3): 305-24; Bartlett J D, Niemann K, Houde B, Allred T, Edmondson M J, Crockett R S.A tolerability study of pirenzepine ophthalmic gel in myopic children. J Ocul Pharmacol Ther. 2003 June;19(3):271-9.).

Further, pirenzepine has been tested in the treatment of diabetes. Issa B G, Davies N, Hood K, Premawardhana L D, Peters J R, Scanlon M F. Effect of 2-week treatment with pirenzepine on fasting and postprandial glucose concentrations in individuals with type 2 diabetes. Diabetes Care. 2003 May;26(5):1636-7. Taken together, these studies show that pirenzepine is a relatively safe compound.

There is no evidence for a neuroprotective or cytoprotective role of muscarinic receptors. Only their role in modulating potentially excitotoxic glutamate release has been discussed (e.g. Sholl-Franco A, Marques P M, Ferreira C M, de Araujo E G.IL-4 increases GABAergic phenotype in rat retinal cell cultures: involvement of muscarinic receptors and protein kinase C. J Neuroimmunol. 2002 December;133(1-2):20-9. Calabresi P, Picconi B, Saulle E, Centonze D, Hainsworth A H, Bernardi G.Is pharmacological neuroprotection dependent on reduced glutamate release? Stroke. 2000 March;31(3):766-72; discussion 773). Muscarinic receptors modulate the mRNA expression of NMDA receptors in brainstem and the release of glutamate. The central role of glutamate receptors in mediating excitotoxic neuronal death in stroke, epilepsy and trauma has been well established. Although calcium ions are considered key regulators of excitotoxicity, new evidence suggests that specific second messenger pathways rather than total $Ca^{2+}$ load are responsible for mediating neuronal degeneration. Evidence exists showing that inhibiting signals downstream of glutamate receptors, such as nitric oxide and PARP-1 can reduce excitotoxic insult. (Aarts M M, Tymianski M. Molecular mechanisms underlying specificity of excitotoxic signaling in neurons. Curr Mol Med. 2004 March;4(2):137-47). Poly(ADP-ribosyl)ation is an immediate cellular response to DNA damage and is catalyzed by poly(ADP-ribose) polymerase (PARP-1). Directly stimulated by DNA breaks, PARP-1 is involved in a variety of physiological and pathophysiological phenomena. Physiologically it is important for maintaining genomic stability. Pathophysiologically, PARP-1 overactivity contributes to a number of diseases associated with cellular stress. Proteolysis of PARP is along with fragmentation of DNA one of the hall marks of apoptosis. PARP is a DNA damage sensor enzyme that normally functions in DNA repair, but promotes cell death when extensively activated by DNA damage, which leads to cell dysfunction and cell death mainly due to depletion of $NAD^+$ (the substrate of PARP-1) and ATP. Overactivation of PARP appears to be prominent in vascular stroke and other neurodegenerative diseases causing necrotic neural death. Therefore PARP inhibitors have drawn intense interest in the recent past as potential cyto-/neuroprotective lead structures with a broad based therapeutic potential, in particular of PARP-1 inhibitors (e.g. Cosi C, Guerin K, Marien M, Koek W, Rollet K. The PARP inhibitor benzamide protects against kainate and NMDA but not AMPA lesioning of the mouse striatum in vivo. Brain Res. 2004 Jan. 16;996 (1):1-8. Suh S W, Aoyama K, Chen Y, Garnier P, Matsumori Y, Gum E, Liu J, Swanson R A. Hypoglycemic neuronal death and cognitive impairment are prevented by poly(ADP-ribose) polymerase inhibitors administered after hypoglycemia. J Neurosci. 2003, 23:10681-90. Pogrebniak A, Schemainda I, Pelka-Fleischer R, Nussler V, Hasmann M.Poly ADP-ribose polymerase (PARP) inhibitors transiently protect leukemia cells from alkylating agent induced cell death by three different effects. Eur J Med Res. 2003 Oct. 22;8(10):438-50. PRE-CLINICAL TRIALS are initiated from various companies: INOTEK PHARMACEUTICALS, USA, http://www.inotekcorp.com/news/index.htm; Guilford Pharmaceuticals Inc. http://www.guilfordpharm.com/etc.

Some additional evidence points towards a crucial role, of PARP1 not only in neuroprotection and repair, but also in memory formation. Cortical cultures derived from PARP1-knockout mice, or cultures treated with a PARP1 inhibitor, are largely resistant to hypoglycaemic neuronal death. Very new findings even indicate a role of PARP1 on formation of long term memories (Suh et al., J. Neurosci. 23 (2003), 10681-10690; Ghen-Ammon et al., Science 304 (2004), 1820-1822).

At present less than 10 PARP-1 inhibitors are in development, although none have yet entered the clinic. Since this class has implications for a variety of serious diseases, most of which represent unmet markets, the further development of molecules such as PJ34 offers considerable clinical and financial promise. (http://www.bioportfolio.com/LeadDiscover /PubMed-030215.htm; Faro R, Toyoda Y, McCully J D, Jagtap P, Szabo E, Virag L, Bianchi C, Levitsky S, Szabo C, Selike F W. Myocardial protection by PJ34, a novel potent poly (ADP-ribose) synthetase inhibitor. Ann Thorac Surg. 2002. 73:575-81).

However, there appears to be a critical balance of the cell death preventing effects of PARP inhibitors, which are mediated by their ability to maintain independently cellular energy metabolism, to inhibit the activation of endonucleolytic DNA degradation and to prevent cell blebbing and toxic profiles of individual PARP inhibitors.

Using a functional cellular model of neuroprotection and a set of neuronal biomarkers a screening of test compounds for novel neuroprotective modes of action was carried out. Surprisingly, it was found that pirenzepine and related compounds have a previously unknown mode of action as PARP inhibitors or PARP binding molecules. Due to these previously unknown neuroprotective effects, the compounds are suitable as cytoprotective and particularly neuroprotective drugs and new lead structures for the development and optimization of related compounds with a dual, i.e. M1/PARP1 mode of action, generally for cytoprotection and, particularly for the treatment of neurodegenerative disorders.

SIR2 is a protein linked to increased lifespan in yeast and the microscopic worm Caenorhabditis elegans, potentially delaying the degeneration of ailing nerve cell branches, relevant for new treatments of a wide range of neurodegenerative disorders, including Parkinson's disease, Alzheimer's disease, amyotrophic lateral sclerosis (Lou Gehrig's disease), various kinds of neuropathy, and multiple sclerosis. In mouse nerve cells it has been shown that the protein SIRT1, which belongs to a family of proteins known as the SIR2 group, delays the breakdown of axons in nerve cells mechanically cut off from the cell body or exposed to a chemotherapeutic agent. Previously evidence was found that this process of axonal degeneration may be an active self-destructive process that the neuron activates under certain conditions. Increased activation of SIRT1 appears to block some or all of those self-destructive processes. Also the possibility of cancer prevention through drugs that increase the activation of SIR2 proteins is explored (Araki T, Sasaki Y, Milbrandt J. R. Increased nuclear NAD biosynthesis and SIRT1 activation prevent axonal degeneration. Science. 2004, 305:1010-3.

There is considerable attention to potential cross-talk between PARP1 and SIR2 proteins: PARP-1 is thought to safeguard genomic integrity by limiting sister chromatid exchanges, with cell death as a consequence of overstimulation of PARP-1 by extensive DNA damage. Prolonged PARP-1 activation depletes $NAD^+$, a substrate, and elevates nicotinamide, a product. The decline of $NAD^+$ and the rise of nicotinamide may downregulate the activity of the SIR2 $NAD^+$-dependent deacetylases, because deacetylation by SIR2 is dependent on high concentration of $NAD^+$ and inhibited by physiologic level of nicotinamide. The possible linkage of the two ancient pathways that mediate broad biological activities may spell profound evolutionary roles for the conserved PARP-1 and SIR2 gene families in multicellular eukaryotes. (Zhang, J. Bioessays, 25 (2003), 808-814).

Surprisingly, it was further found that pirenzepine and related compounds have a previously unknown mode of action as SIR2 modulators, e.g. SIR2 binding molecules. Due to these previously unknown neuroprotective effects, the compounds are suitable as cytoprotective and particularly neuroprotective drugs and new lead structures for the development and optimization of related compounds with a combined, i.e. M1/PARP1/SIR2 mode of action, generally for cytoprotection and particularly for the treatment of neurodegenerative disorders.

Taken together, the above discussion shows that PARP activity is important for cytoprotective, particularly neuroprotective processes. The general feature of the neuronal challenges as shown in the examples below, is an initial calcium overload leading to apoptotic cell death which can be prevented or delayed by application of pirenzepine and related compounds, like LS-75 (PBD). We show that also in an experimental model for non-neuronal inflammatory processes, like LPS challenge of 3T3 fibroblasts, the compounds have a cytoprotective effect. This effect is accompanied by corresponding changes of apoptotic markers and inflammatory markers, monitored by staining Western blots with antibodies against PARP-1 and Cox-2.

Thus, a first aspect of the present invention relates to the use of a compound of formula I

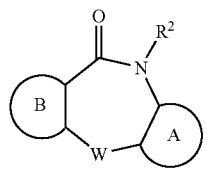

wherein A and B are five- or six-membered rings optionally containing at least one heteroatom selected from N, S and O, wherein the rings are optionally mono- or polysubstituted with halo, e.g. F, Cl, Br, or I, $C_1$-$C_4$-(halo)-alkyl, $C_1$-$C_4$-(halo)-alkoxy, amino, $C_1$-$C_4$-alkyl-amino, or di($C_1$-$C_4$-alkyl) amino, W is S, O, $NR^1$ or $CHR^1$ R1 is hydrogen, Y or COY, R2 is hydrogen or $C_1$-$C_4$-(halo)-alkyl, and Y is $C_1$-$C_6$ (halo)alkyl, or $C_3$-$C_8$ cyclo-(halo)-alkyl, wherein the alkyl or cycloalkyl group is optionally substituted with a five- or six-membered ring optionally containing at least one heteroatom selected from N, S and O, and wherein the ring is optionally mono- or poly-substituted with halo, $C_1$-$C_4$-(halo)alkyl, $C_1$-$C_4$(halo)alkoxy, amino, $C_1$-$C_4$-alkyl amino, di($C_1$-$C_4$-alkyl)amino or Z, wherein Z is a $C_1$-$C_6$ (halo) alkyl group co-substituted with a group $N(R4)_2$, wherein each R4 is independently hydrogen, $C_1$-CB alkyl, or CO-$C_1$-$C_8$-alkyl or wherein both R4 together form a five- or six-membered ring optionally containing at least one further heteroatom selected from N, S and O, wherein the ring is optionally mono- or polysubstituted with halo, $C_1$-$C_4$ (halo)-alkyl and $C_1$-$C_4$(halo) alkoxy, or of a salt or derivative thereof for the manufacture of a cytoprotective medicament, particularly a neuroprotective medicament.

The term "(halo)alkyl" according to the present invention relates to an alkyl group which optionally contains at least one halo, e.g. F, Cl, Br or I substituent up to perhalogenation. The term "salt" preferably refers to pharmaceutically acceptable salts of compounds of Formula I with suitable cations and/or anions. Examples of suitable cations are alkaline metal cations such as $Li^+$; $Na^+$ and $K^+$, alkaline earth metal cations such as $Mg^+$ and $Ca^+$ as well as suitable organic cations, e.g. ammoniums or substituted ammonium cations. Examples of pharmaceutically acceptable anions are inorganic anions such as chloride, sulfate, hydrogen sulfate, phosphate or organic cations such as acetate, citrate, tartrate, etc.

Derivatives of compounds of Formula I are any molecules which are converted under physiological conditions to a compound of Formula I, e.g. esters, amides etc. of compounds of Formula I or molecules which are products of metabolization reactions of a compound of Formula I.

Preferably, the compounds of Formula I are used for the prevention or treatment of neurologic PARP-1 and/or SIR2-associated disorders, i.e. disorders which are caused by and/or accompanied by PARP-1 dysfunction, particularly a dysfunctional increase in PARP-1 activity, and/or disorders which are caused by and/or accompanied by SIR2-dysfunction, particularly a dysfunctional increase in SIR2 activity. For example these disorders are neurodegenerative or neuroinflammatory conditions in disorders such as dementia, Parkinson, Alzheimer, stroke, schizophrenia, epilepsy, etc. The compounds of the invention are particularly effective in disorders of the central nervous system, e.g. the brain including traumatic brain injuries, even to contralateral areas of the brain thereby preventing or inhibiting secondary neurodegeneration. The compounds are also useful as neuronal repair agents and in the improvement of memory formation, e.g. in the formation of long-term memories. Further, the compounds are suitable for treatment or prevention of ulcerative and other inflammatory conditions of the gastrointestinal system.

Still a further preferred indication is for the prevention or treatment of pain, e.g. chronic neuropathic pain, because proapoptotic mechanisms play a role in initial phases of various forms of chronic pain (Malone S et al. Apoptotic genes expression in the lumbar dorsal horn in a model neuropathic pain in rat. Neuroreport 2002 Jan. 21; 13(1): 101-6)

Still, a further preferred indication is for the prevention or treatment of neurological or neuron-associated ocular disorders.

For therapeutic applications, the compounds of Formula I may be used alone or together with other medicaments, e.g. clozapine, olanzapine, antidiabetic or anticancer treatments.

In the compounds of Formula I, the cyclic groups A and B are preferably selected frm

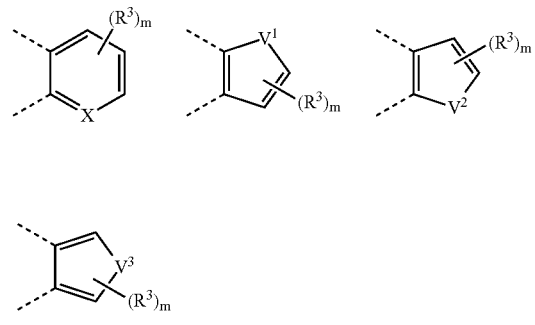

wherein X is CH, N, or CR3,

V1, V2 or V3 are selected from —O—, —S—, and NR6,

R3 is in each case independently halo, $C_1$-$C_4$-(halo)-alkyl, $C_1$-$C_4$-(halo)-alkoxy, amino, $C_1$-$C_4$-alkyl amino, or di($C_1$-$C_4$-alkyl) amino, m is an integer of 0-2, and R6 is hydrogen or $C_1$-$C_4$-(halo)alkyl.

More preferaby, the cyclic group A is selected from

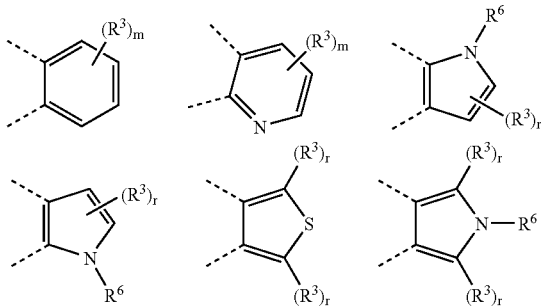

wherein R3 is defined as aboved,
m is an integer of 0-2,
r is an integer of 0-1 and
R6 is hydrogen or methyl.

More preferably, the cyclic-group B is selected from

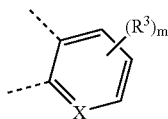

wherein X, R3 and m are as defined above

In one embodiment, R1 is Y. In this case Y is preferably $C^3$-$C^8$ cyclo(halo)-alkyl, e.g. cyclopropyl, cyclobutyl or cyclopentyl.

In a further embodiment, R1 is COY and Y is selected from

—(CHR7)q-R8 wherein R7 is hydrogen, halo or $C_1$-$C_4$-(halo)alkyl,
q is an integer of 1-4, and preferably 1 and
R8 is a five- or six-membered ring optionally containing at least one heteroatom, wherein the ring is optionally mono- or polysubstituted with $C_1$-$C_4$(halo)alkyl or a ω-amino-substituted alkyl group Z as defined above.

In this embodiment, R8 is preferably selected from

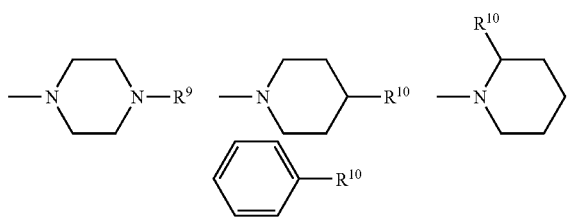

wherein R9 is hydrogen or $C_1$-$C_4$(halo)alkyl and R10 is a ω-amino-substituted alkyl group Z as defined above.

R9 is preferably a methyl group. The ω-amino-substituted alkyl group Z is preferably a $C_1$-$C_4$ (halo)alkyl group having a terminal amino group which is substituted with at least one $C_1$-$C_6$ alkyl group, e.g. a diethylamino, or di-isobutylamino group, or with a CO ($C_1$-$C_6$) alkyl group and with hydrogen or a $C_1$-$C_2$ alkyl group.

Specific examples of compounds of Formula I are pirenzepine and related compounds as disclosed in FR 1,505,795, U.S. Pat. Nos. 3,406,168, 3,660,380, 4,021,557, 4,210,648, 4,213,984, 4,213,985, 4,277,399, 4,308,206, 4,317,823, 4,335,250, 4,424,222, 4,424,226, 4,724,236, 4,863,920, 5,324,832, 5,620,978, 6,316,423, otenzepad and related compounds as disclosed in U.S. Pat. Nos. 3,406,168, 5,324,832 and 5,712,269, AQ-RA741 and related compounds as disclosed in U.S. Pat. Nos. 5,716,952, 5,576,436 and 5,324,832, viramune and related compounds as disclosed in EP-A-0429987, and U.S. Pat. Nos. 5,366,972, 5,705,499, BIBN 99 and related compounds as disclosed in U.S. Pat. Nos. 6,022,683 and 5,935,781, DIBD, telenzepine and related compounds as disclosed in EP-A-0035519, and U.S. Pat. No. 4,381,301 and salts or derivatives thereof. The above documents are herein incorporated by reference.

Further preferred compounds are 7-azabicyclo-[2.2.1]-heptane and heptene compounds such as a tiotropium bromide as disclosed in U.S. Pat. Nos. 5,817,679, 6,060,473, 6,077,846, 6,117,889, 6,255,490, 6,403,584, 6,410,583, 6,537,524, 6,579,889, 6,608,055, 6,627,644, 6,635,658, 6,693,202, 6,699,866 and 6,756,392, heterocyclic compounds, e.g. pyrrolidinones, tetrahydropyridines, isoxazocarboxamides, thienopyrane carboxamides, or benzopyranes, such as alvameline tartrate and related compounds disclosed in U.S. Pat. Nos. 6,306,861, 6,365,592, 6,403,594, 6,486,163, 6,528,529, 6,680,319, 6,716,857 and 6,759,419, metoclopramide and related compounds as disclosed in U.S. Pat. No. 3,177,252 and QNB and related compounds as disclosed in U.S. Pat. No. 2,648,667 and salts and derivatives thereof. The above documents are herein incorporated by reference.

Further, the invention encompasses compounds which are metabolized to give diaryl diazepinones according to Formula I such as clozepine and olenzepine.

A further aspect of the present invention relates to the use of a compound which is a dual M1 muscarinic receptor inhibitor and a PARP inhibitor for the manufacture of a neuroprotective medicament, preferably for the prevention or treatment of disorders as indicated above.

The dual inhibitor compound is preferably a moderately strong PARP inhibitor, which has an $IC_{50}$ value for PARP from 100 to 10000 µM, more preferably from 250 to 1000 µM. The determination of the $IC_{50}$ value is carried out as indicated as in the Examples.

Still, a further aspect of the present invention relates to the use of a compound which is a dual M1 muscarinic receptor inhibitor and a PARP inhibitor and additionally a SIR2 modulator or binding molecule for the manufacture of a neuro- or cytoprotective medicament, preferably for the prevention or treatment of disorders as indicated above.

The compound is preferably a moderately strong PARP inhibitor as indicated above. Further, the compound is preferably a SIR2 inhibitor which has a $IC_{50}$ value for SIR2 from 1 to 10,000 µM, more preferably from 5 to 5,000 µM. The determination of the $IC_{50}$ value is carried out as indicated in the Examples.

The compounds as indicated above are preferably administered to a subject in need thereof as a pharmaceutical composition, which may contain pharmaceutically acceptable carriers, diluents and/or adjuvants. The pharmaceutical composition may be administered in the form of a tablet, capsule, solution suspension, etc. The medicament may be administered according to any known means, wherein oral and intravenous administration is particularly preferred. The dose of the active ingredient depends on the type and the variety of disease and usually is in the range from 1 to 2000 mg/day.

The present application has applications in human and veterinary medicine, particularly in human medicine.

Furthermore, the present invention shall be explained by the following Figures and Examples.

FIGURE LEGENDS

FIG. 1: Synthesis of a pirenzepine-related irreversible affinity-tag (11).

Figure 2B:
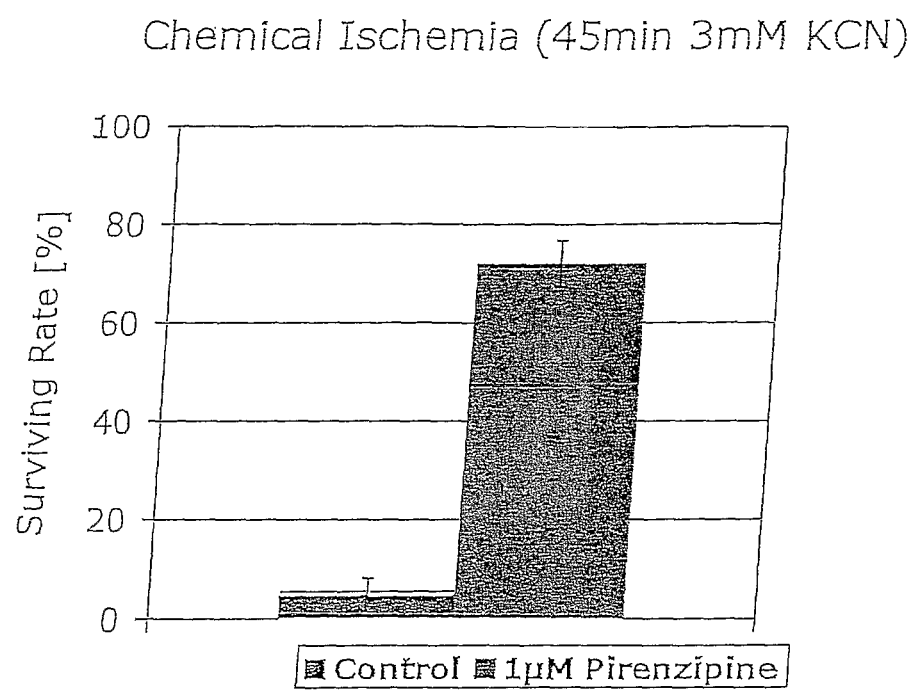
Figure 2D:
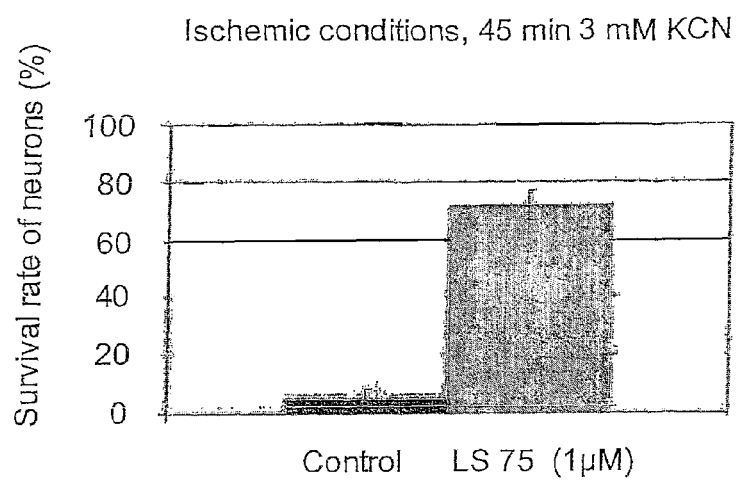
Figure 2E:
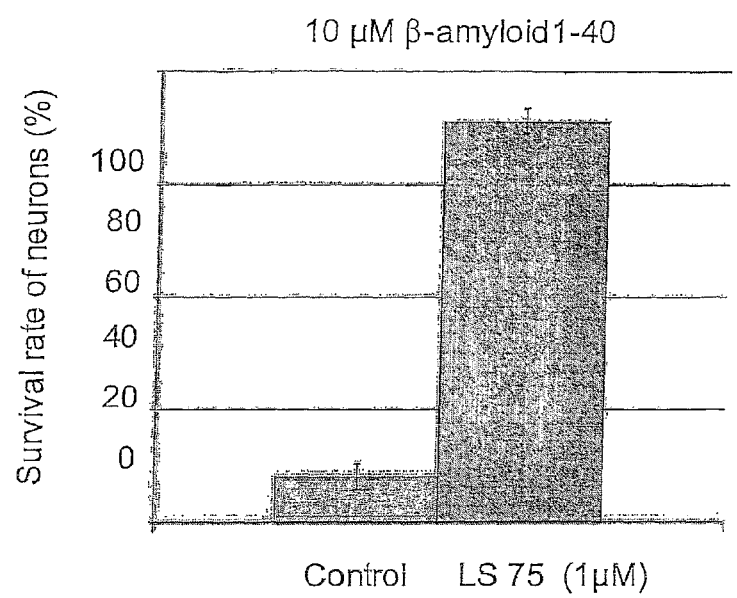

FIG. 2: Chemical structures of pirenzepine and its metabolite LS-75 (FIG. 2a); Example of neuroprotective in vitro effect of 1 μM Pirenzepine, which prevents neuronal death from chemical ischemia under conditions described (FIG. 2b). During the course of ischemic insult or respective rescue by LS-75, concentrations of apoptotic and inflammatory markers, PARP-1, Cox-2 and iNOS were quantified by corresponding Western blots (FIG. 2c). The survival of neurons in the presence of pirenzepine and LS-75 after challenge with KCN (45 min 3mM KCN) and β-amyloid (10 μM β-amyloid 1-40) is shown (FIGS. 2d and e). A summary of these experiments after three different challenges (excitotoxic, ischemic and β-amyloid-induced in terms of neuroprotective EC50-values of pirenzepine and LS-75 is shown (FIG. 2f).

Figure 3:
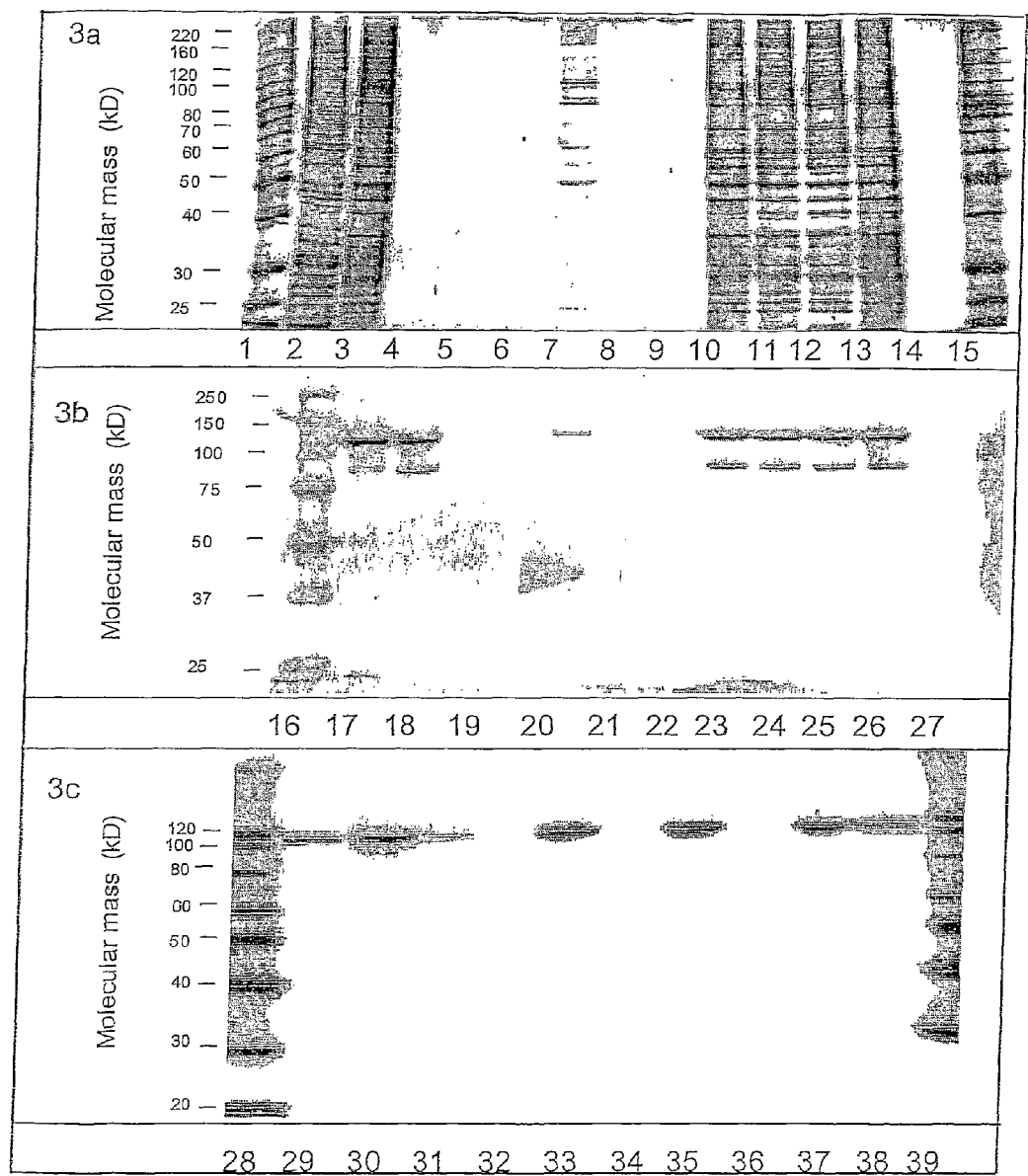

FIG. 3: The silver staining of 1D gels of fractions obtained after affinity enrichment is shown in FIG. 3a: lanes 1-6, 8-17 are controls, lane 7 is the pirenzepine affinity tag enriched material with prominent bands at 113 and 89 kD and a weak band at 110 kD; 3b: Immunostaining of 1D gels of extracts of V56 cells with a specific anti PARP-1 antibody. Lane 16 is an All Blue Marker, 17 is an urea extract and 18 a NP-40 extract; lanes 19-22 are eluates from the pirenzepine-affinity column: 3c: The pirenzepine-affinity tag prepared according to the Methods section irreversibly binds to SIR-2 and provides enrichment of the protein, as demonstrated by immunostaining 1D gels of extracts of V56 cells with a specific anti SIR-2 antibody. Lanes 28 and 39 are molecular weight markers: 29 and 38 are raw extract; 30/31: eluate 1 and flow through 1 after overnight incubation of extracts with irreversible pirenzepine-affinity tag, 32/33: Control, over night incubation of raw extract with streptavidin agarose beads blocked with irreversible pirenzepine affinity tag; 34/35: Control, over night incubation of raw extract with 5'-AMP-Sepharose beads (Sigma, A3019); 36/37: Control, over night incubation of raw extract without streptavidin agarose beads coupled to irreversible pirenzepine-affinity tag.

Figure 4:
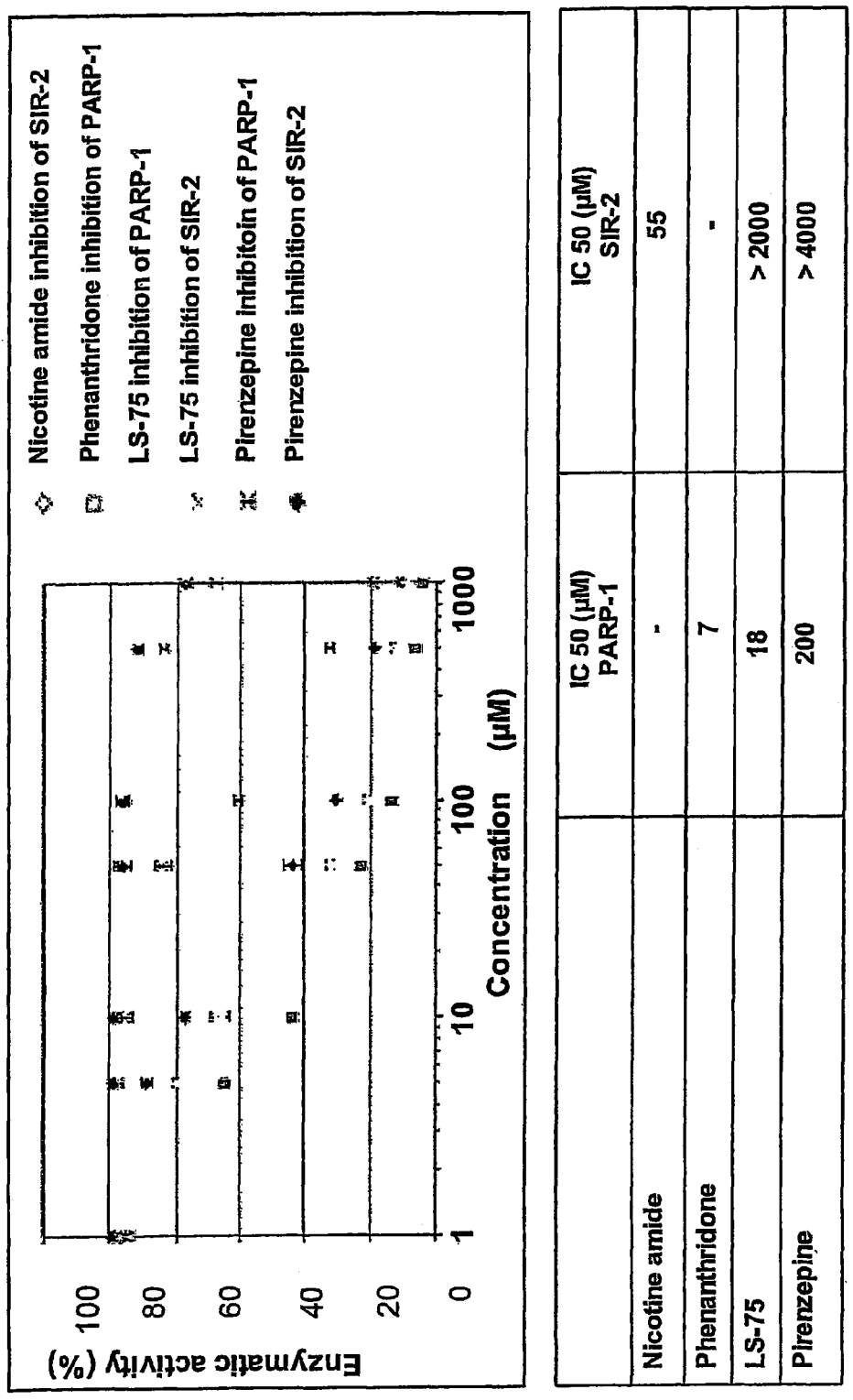

FIG. 4: Inhibiton of SIR-2 and PARP-1 by pirenzepine and its derivative LS-75:

In the upper part the corresponding enzymatic activites are plotted against increasing concentrations of Pirenzepine and LS-75. As negative controls, phenanthridone as a typical PARP-1 inhibitor and nicotine amide as a typical SIR-2 inhibitor were employed (FIG. 4a). The table in the lower part of the figure shows respective IC50-values for all substances, LS-75 appears to be a moderately strong PARP-1 inhibitor. Pirenzepine is a rather weak PARP-1 inhibitor. Both substances are weak SIR-2 inhibitors (FIG. 4b).

Figure 5:
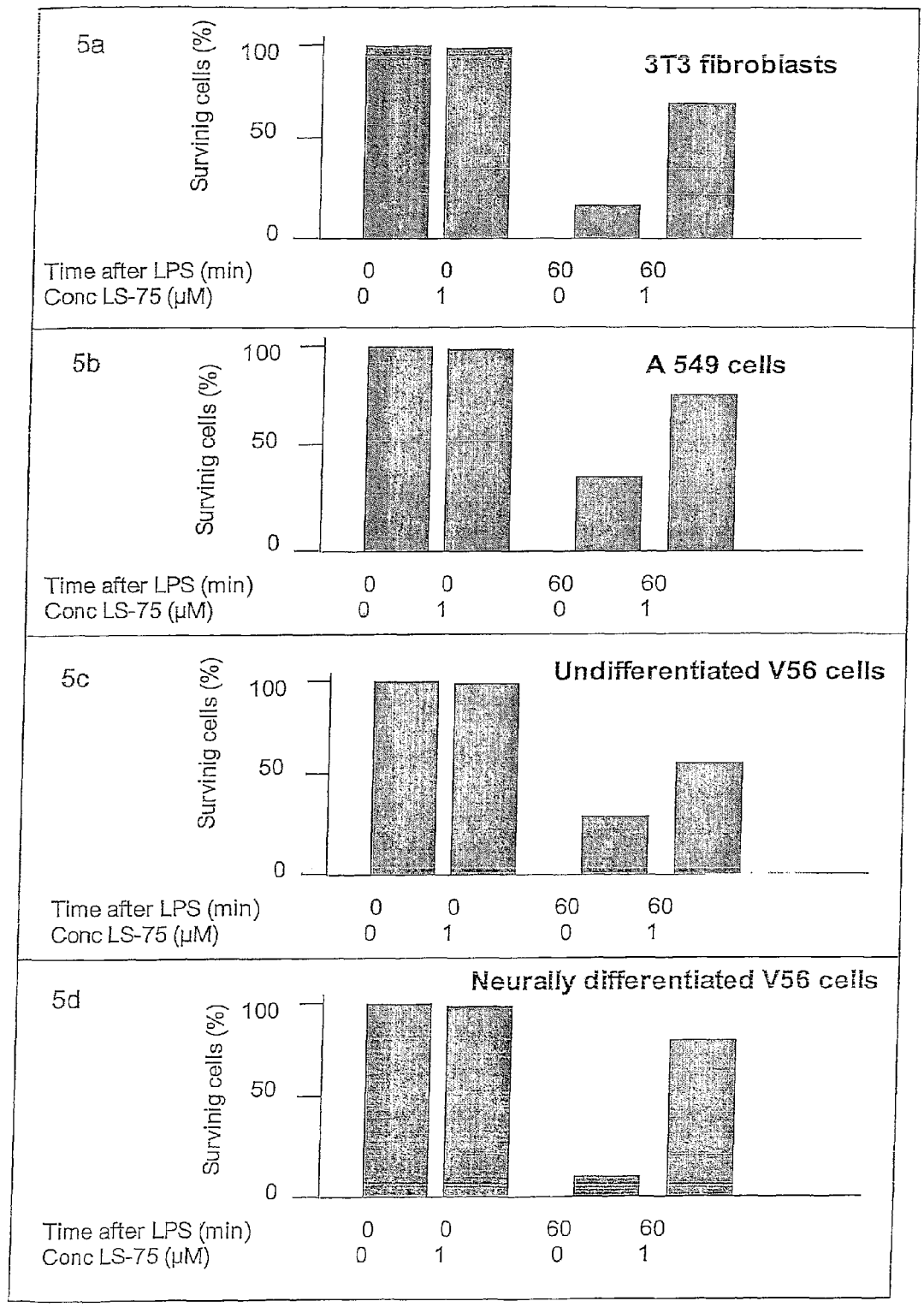

FIG. 5: Pirenzepine and LS-75 (shown here) protect from LPS challenge (100 ng/ml for 60 min): 5a protection of 3T3 fibroblasts; 5b protection of A 549 cells; 5c protection of undifferentiated V56 embryonic stem cells; 5d of neurally differentiated V56 embryonic stem cells.

Figure 6:
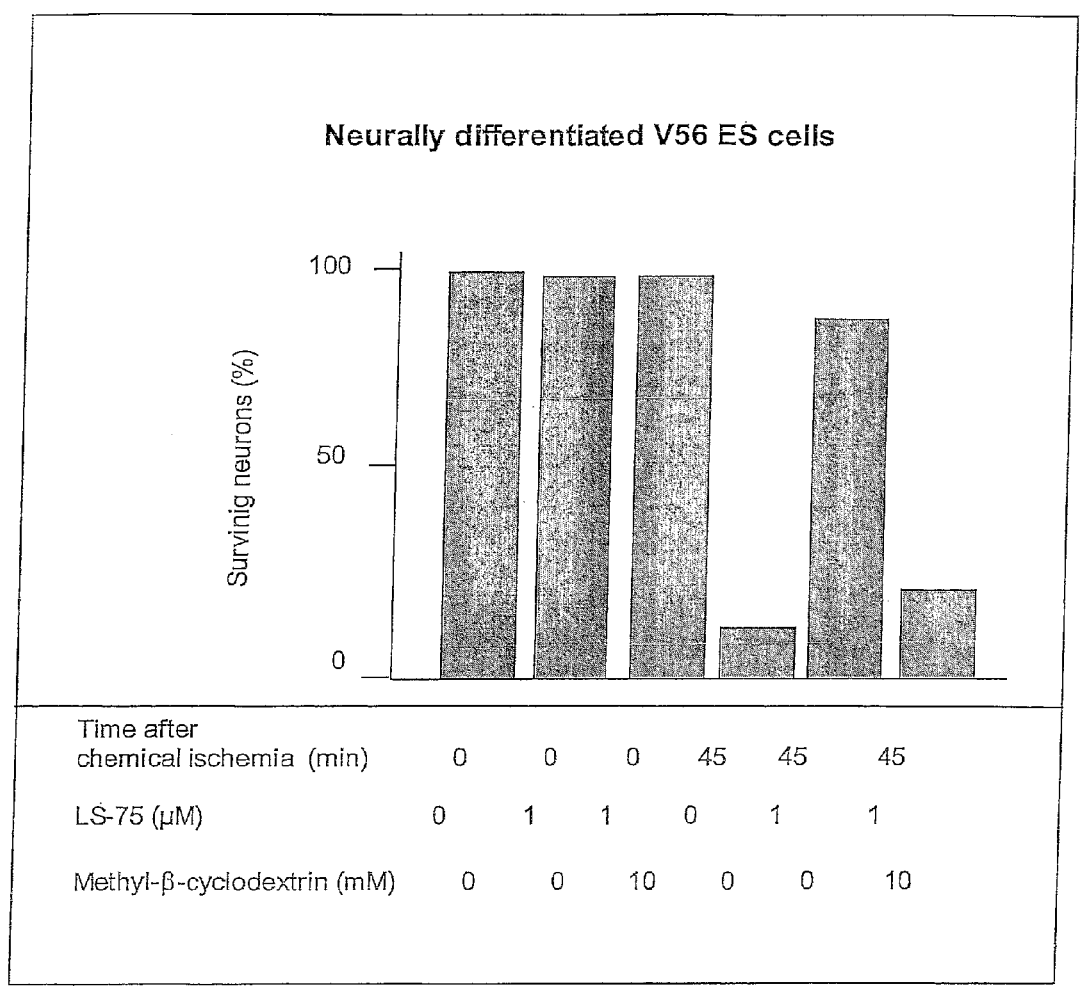

FIG. 6: Effects of Pirenzepine and LS-75 (shown here) are dependent on the presence of cholesterol-rich lipid rafts. Established methods of disruption of these rafts by cholesterol depletion by addition of methyl-β-cyclodextrin decreases the neuro protective effect (and also the general cytoprotective effect, not shown).

Figure 7:
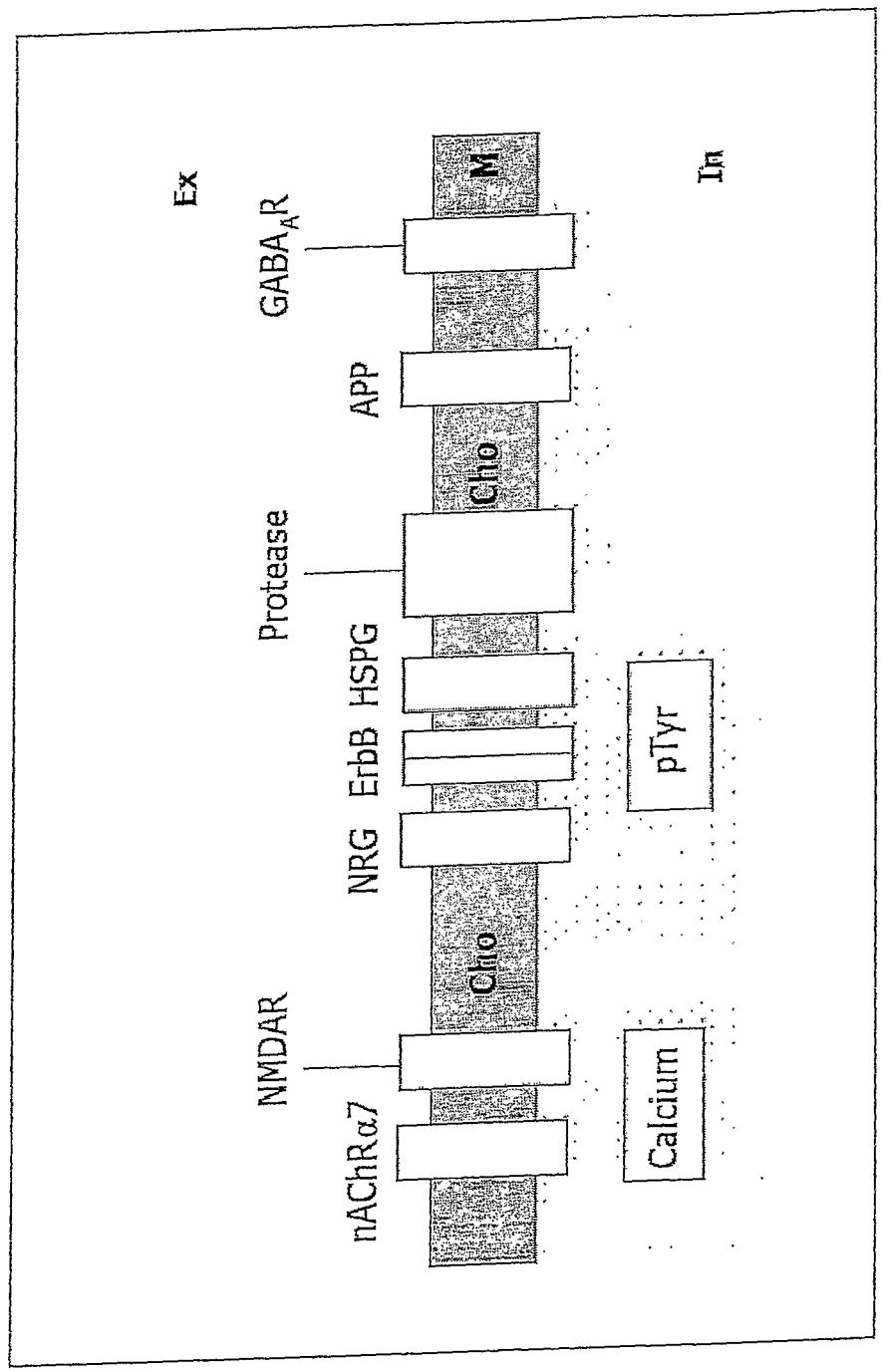

FIG. 7: Organisation and components of neuronal lipid rafts:

These functional membrane compartments are organised by the activity-dependent interaction of neuregulin (NRG), heparansulfate binding proteins (HSPG) and dimeric ErbB receptors (ErbB) which regulate the assembly and activity of a specific set of membrane proteins, which are essential for some of the most important neurophysiological/neuropathological processes. Some of them have been identified recently as genetic risk factors for Alzheimer's disease (marked AD) and /or schizophrenia (SCH). nAChRa7 is a nicotinic acetylcholine receptor isoform (AD,SCH), NMDAR is an ionotropic glutamate receptor isoform, NRG is a neuregulin (AD, SCH), APP is the amyloid precursor protein (AD), $GABA_AR$ is the γ-aminobutyric acid-gated chloride-channel; pTyr stands for phospho-tyrosine; Cho: the raft lipids contain cholesterol (relates to ApoE4, risk factor for AD) and sphingolipids Ex: extracellular; M: membrane compartment; In: intracelluar; Lipid rafts also play a role in non-neuronal cells and mechanisms generally related to inflammation and apoptosis.

Figure 8:
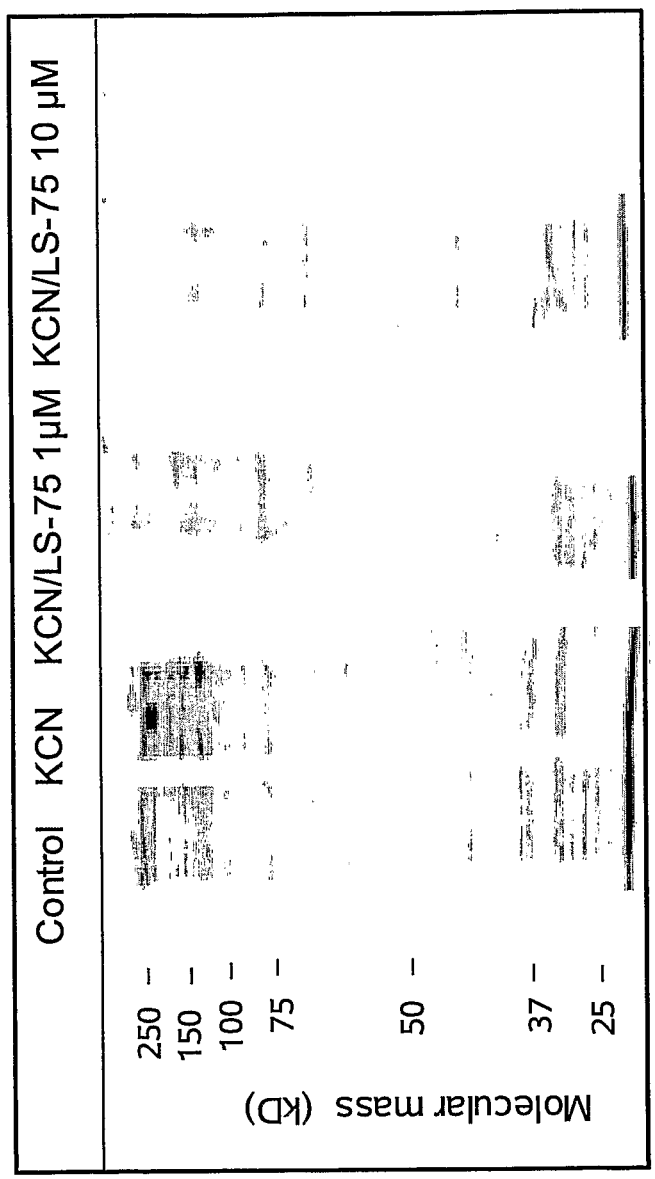

FIG. 8: LS-75 prevents poly-ADP-ribosylation under cellular conditions:

The ischemic insult of neural cells by KCN/glucose deprivation induces a substantial increase in of staining with this antibody, in particular of a host of proteins in the 100-250 kD range. This effect is reversed by addition of neuroprotective concentrations of LS-75; here we show the decrease of poly-ADP-ribosylated proteins during ischemic insult by the presence of 1 and 10 μM LS-75, respectively. The IC 50 of these effects lies below 1 μM (approx. 0.3 μM).

Figure 9:
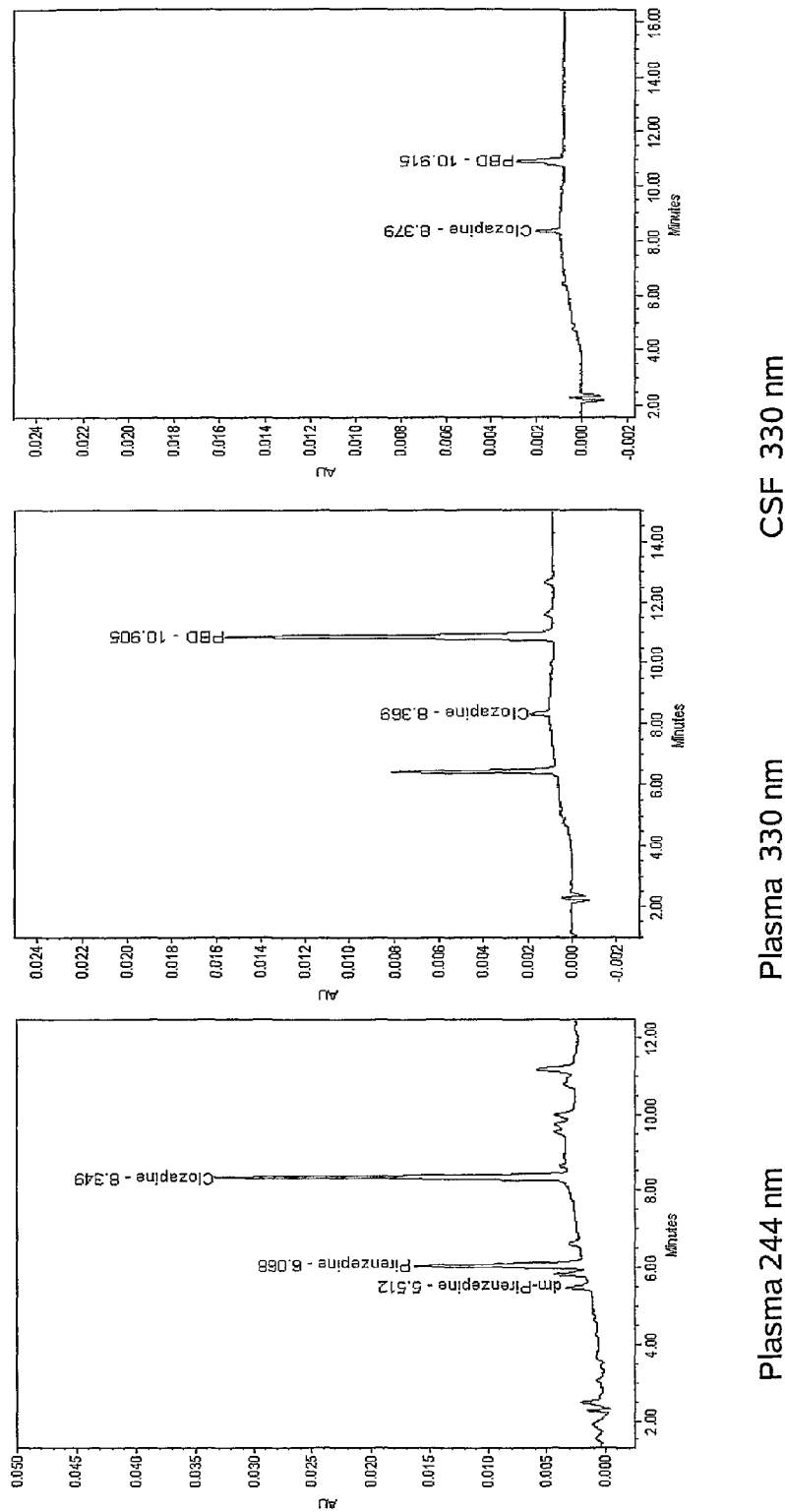

FIG. 9: Determination of concentrations of Pirenzepine and its two main metabolites desmethyl-Pirenzepine (dm-Pirenzepine) and LS-75 (PBD) in plasma and cerebro-spinal fluid (CSF) by HPLC and ultraviolet absorbance detection; AU are arbitrary units; Pirenzepine and dm-Pirenzepine are detected at 244 nm; LS-75 (PBD) is detected at 330 nm; clozapine which absorbs at both wave lengths is always used as internal standard; The respective retention times are indicated in minutes next to corresponding peaks.

Figure 10:
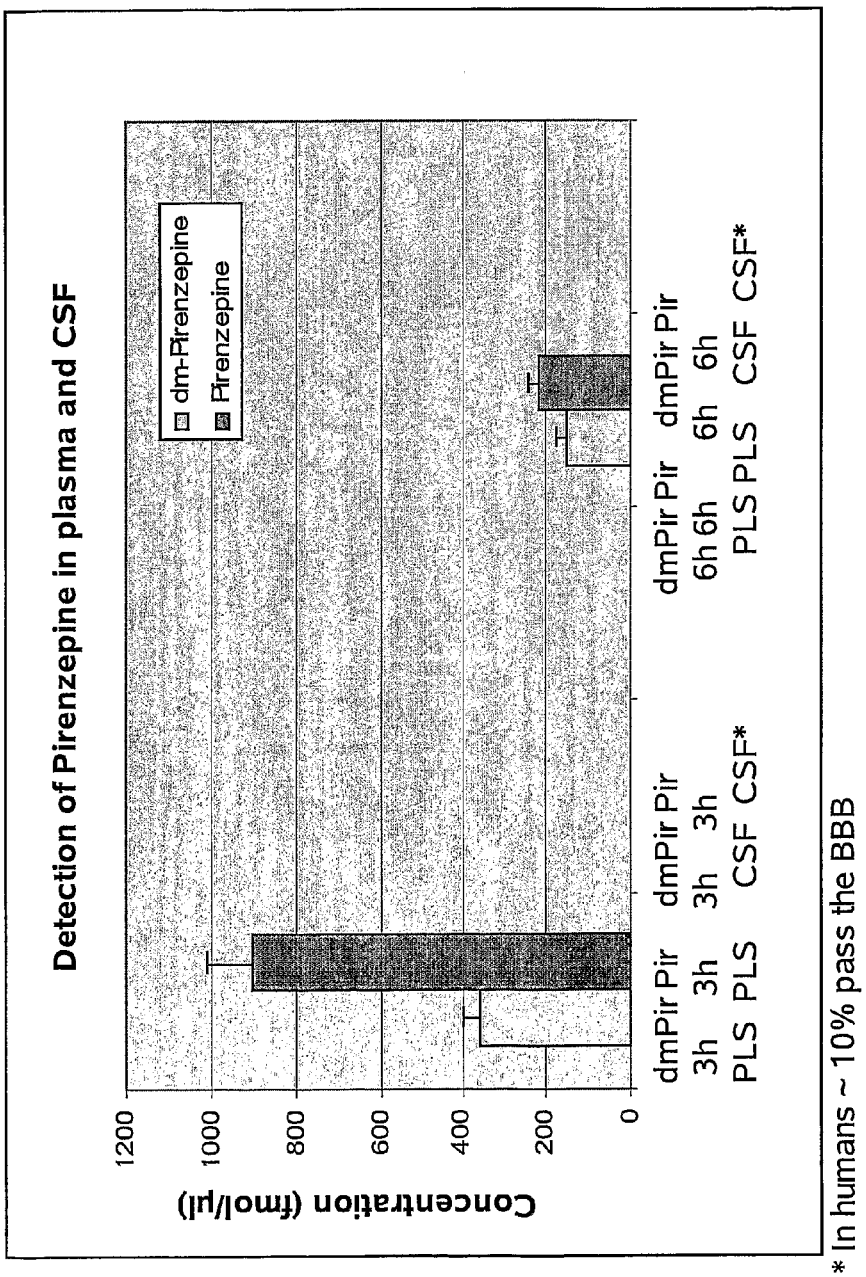

FIG. 10: The peak concentrations of Pirenzepine and dm-Pirenzepine are reached about 3 h after oral application of 50 mg Pirenzepine, the left part of the graph shows corresponding concentrations in plasma (PLS) and cerebrospinal fluid (CSF) of test rats after 3 h, the right part after 6 h, respectively.

Figure 11:
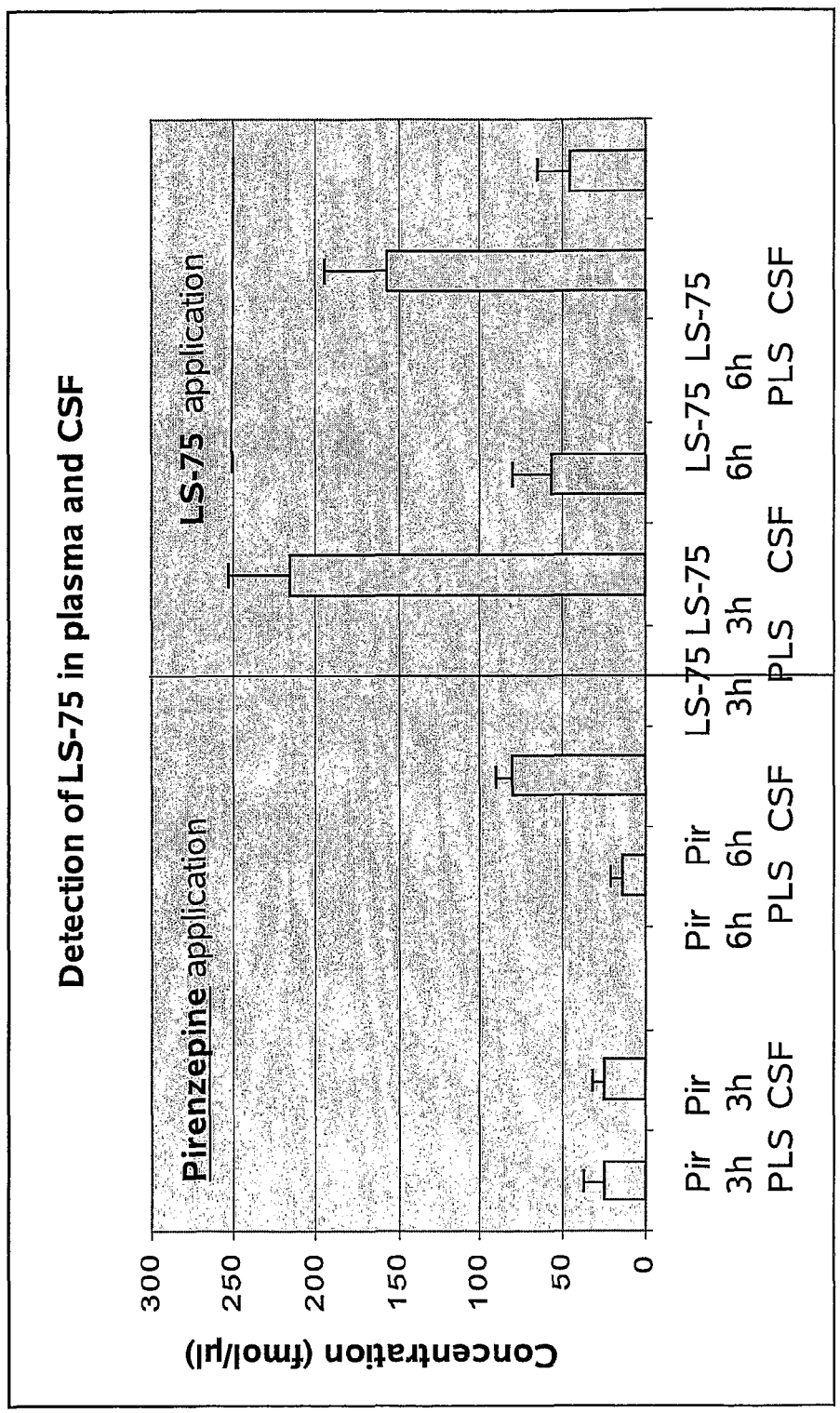

FIG. 11: Detection of LS-75 in plasma and CSF of test animals shows that the substance passes the blood-brain-barrier (BBB) and is enriched in the brain after Pirenzepine application. The left part of FIG. 11 shows LS-75 concentrations in plasma (PLS) and CSF after three and six hours: after 6 h there is a substantial increase of LS-75 levels in CSF; in the left part LS-75 concentrations after application of LS-75 (3 and 6 h later) are shown: 25-30% of LS-75 pass through the blood-brain-barrier.

Figure 12:
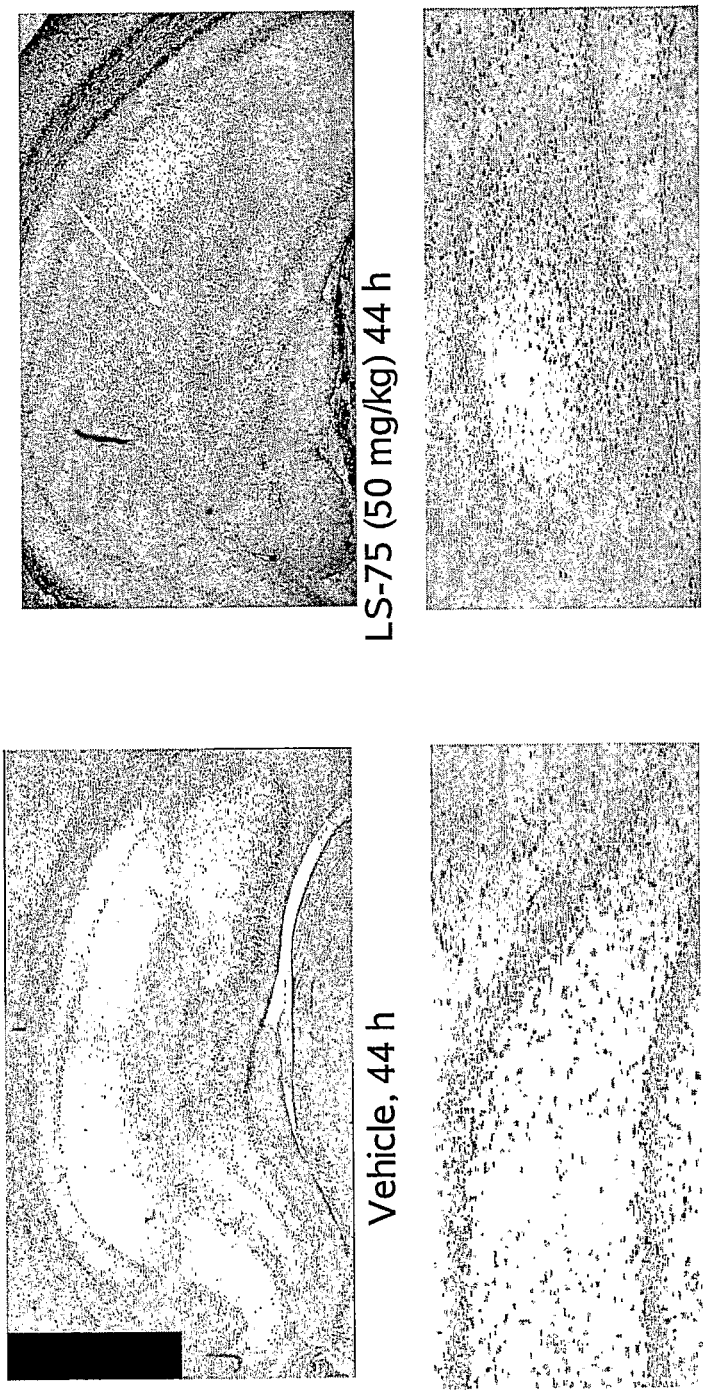
Figure 13:
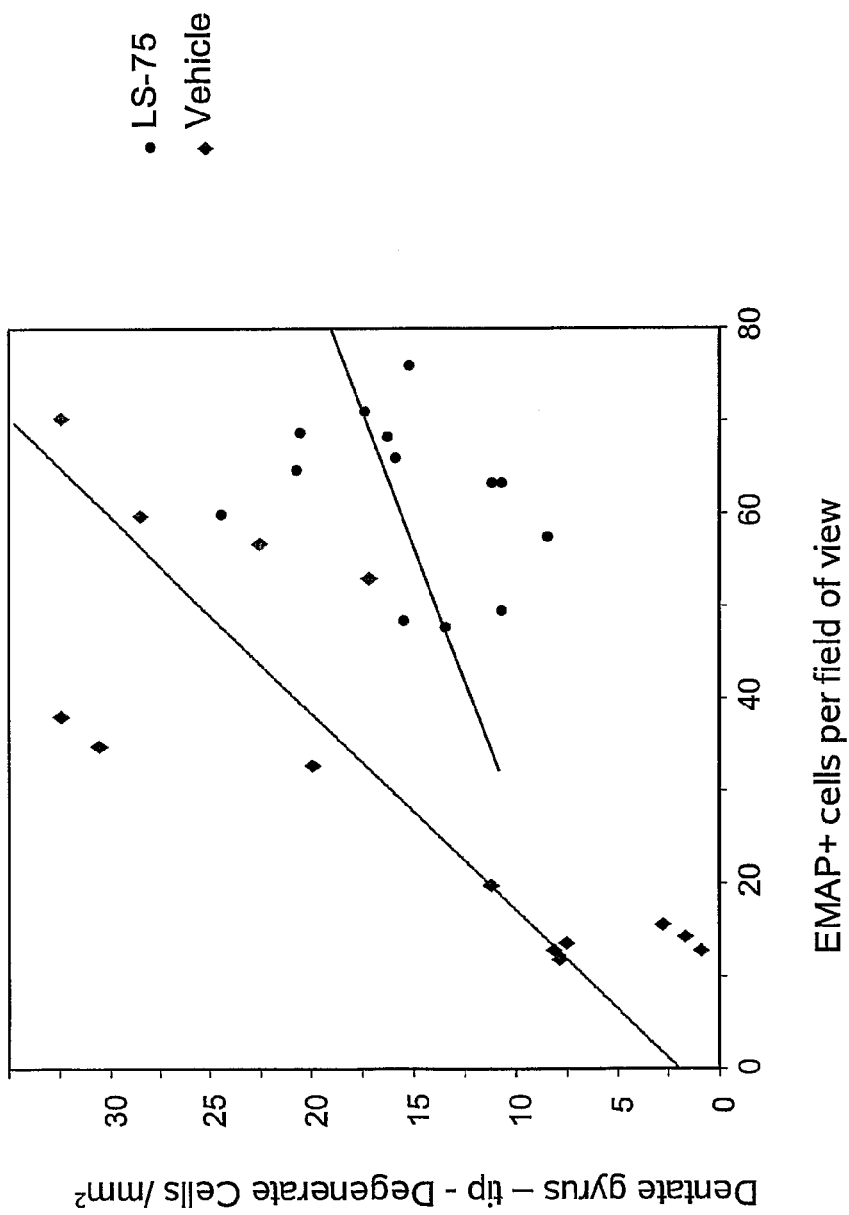

FIGS. 12 and 13: Controlled Cortical Impact Injury (CCI) (Craniotomy, metallic piston on dura) trauma associated disorganisation was assessed in terms of protective effects: Markers for cell damage (fast luxol blue and EMAP) reduced by 40-60% in LS-75 treated animals as compared to controls, in the contralateral hippocampus.

EXAMPLES

Example 1

PARP1 Inhibition
1. Materials and Methods
1.1 Biological test system: Cell culture model for chemical ischemia and neuroprotection For all experiments, D3 embryonic stem (ES) cells derived from 129/sv mice [Okabe et al., 1996] were cultivated for 12 days, with passages on days 2, 4, 7 and 9 as described previously [Sommer et al., 2004]. Insult conditions: Cells (24-well plates) were pre-incubated with or without 20 nM EPO in fresh medium for 24 hours at 37° C. Cells were rinsed once with low $K^+$ solution (140 mM NaCl, 4.7 mM KCl, 1.2 mM $KH_2PO_4$, 2.5 mM $CaCl_2$, 1.2 mM $MgSO_4$, 11 mM glucose, 15 mM Hepes-NaOH, pH 7.35). Cells (either with or without EPO pre-incubation) were incubated for up to 45 min (37° C.) with either low $K^+$ solution or with glucose-free low $K^+$ solution supplemented with 1 mM KCN (chemical ischemia solution [Kume et al., 2002]). Vitality control to asses numbers of surviving neurons was performed by a brief stimulation with a low dose of glutamate (10 µM). Afterwards, cells were washed three times with ice cold phosphate buffered saline (PBS), and then proteins were harvested. Suspended cells were pelleted at 500×G, and lysed into 9M urea 4% CHAPS. The cell lysate was desalted with a NAP-10 column (Amersham Biosciences), preequilibrated with the same buffer, and protein content was determined.

1.2 Calcium-Imaging

Functional tests by calcium imaging were performed essentially as described [Sommer et al., 2004]. Briefly, cells were loaded with 2 µM of fura-2 AM in DMEM for 45 min at 37° C. in the dark. Measurements of relative changes in $[Ca^{2+}]$ were made on an inverted epifluorescence microscope (Olympus IX70 S1F2) with a Polychrom IV Monochromator (Xe-lamp, USHIO). Excitation wavelengths ($\lambda_1, \lambda_2$) and the emission wavelength were 340, 380 and 510 nm, respectively. Acquisition and analysis of data after appropriate stimulation were performed by using MetaFluor software (Universal Imaging Corporation). Image resolution was 168×129 pixels (binning 8×8, pixel size 6.8×6.8 µm). Only cells identified as neurons by morphological criteria and occasional immunostaining (not shown) and those whose calcium levels returned to the resting state after the first stimulation were taken into account. Controls included nominal zero calcium (negative) and 5 µM ionomycin (positive), 10 µM glutamate (positive) and depolarisation (55 mM K+) (positive). Pharmacological agents were applied by a multi-valve, single-output focal drug application device (ALA Scientific) with the perfusion system DAD-12. Ratio images were displayed as a percentage of relative change in fluorescence over background fluorescence scale for comparison across experiments [as described in Sommer et al., 2004]. During each stimulation event 20 image pairs were acquired.

1.3 Chemical Proteomics; Synthesis of Pirenzepine-affinity Tag

Pirenzepine was used as a starting structure for the synthesis of an irreversible, i.e. covalently attached, affinity reagent (Fishhook) for target proteins. A reactive —SCN group is introduced which binds to lysines in or near the binding site of the compound. A biotinylated linker serves for enrichment of bound protein. The synthesis is described in FIG. 1.

1.3.1 Synthesis of 2-nitro-N-(2-chloro-pyridin-3-yl)-benzamide, (3)

A solution of 2-nitrobenzoylchloride (7.2 g) in 100 ml toluene was added dropwise to a stirring solution of 2-chloro-3-amino-pyridine (10.0 g) in 100 ml toluene. After the entire amount was added, the mixture was heated to 80° C. for 120 min. After the reaction mixture was cooled down and the resulting 2-nitro-N-(2-chloro-pyridin-3-yl)-benzamide was isolated by filtration. Yield 10.0 g, mp 158-161° C.

1.3.2 Synthesis of 2-amino-N-(2-chloro-pyridin-3-yl)-benzamide, (4)

Stannous chloride (60.0 g, 320 mmol) was added in the solution of 2-nitro-N-(2-chloro-pyridin-3-yl)-benzamide (14.0 g) in absolute ethanol (200 mL). After being refluxed for 4 hours the solution was diluted with 160 ml conc. HCl and left in the refrigerator to crystallize. Obtained product was isolated by filtration. Isolated substance was dissolved in 100 ml boiling water and made alkaline with 30% NaOH (pH 8.5). Obtained precipitate was isolated by filtration and dried. Yield 7.0 g, mp 172-175° C.

1.3.3 Synthesis of 5,11-Dihydro-benzo[e]pyrido[3,2-b][1,4]diazepin-6-one, (5)

2.5 g of 2-nitro-N-(2-chloro-pyridin-3-yl)-benzamide were heated to 210° C., accompanied by stirring, and as soon as the evaporation of hydrogen chloride began, the source of heat was withdrawn, and the molten mass was allowed to cool while stirring. The cool solidified mass was pulverized and was then dissolved in 150 ml boiling ethanol to which 0.5 ml of an aqueous 30% solution of sodium hydroxide had been added. After cooling the product crystallized out. Yield 1.2 g, mp 278-280° C.

1.3.4 Synthesis of 11-(2-Chloro-acetyl)-5,11-dihydrobenzo[e]pyrido-[3,2-b][1,4]diazepin-6-one, (6)

5,11-Dihydro-benzo[e]pyrido[3,2-b][1,4]diazepin-6-one (970 mg) was refluxed for 10 min with 15 ml dry dioxane. Thereafter acetylylchloride (565 µl) and triethylamine (1.05 ml) was simultaneously added (dropwise) over 45 min. Reaction mixture was refluxed with stirring for another 8 hrs. It was vacuum filtrated after cooling. The filtrate was evaporated in vacuo, and the residue recrystallized from acetonitrile after being treated with activated charcoal. Yield 1.10 g.

1.3.5 Synthesis of 4-[2-Oxo-2-(6-oxo-5,6-dihydro-benzo[e]pyrido-[3,2][1,4]diazepin-11-yl)-ethyl]-piperazine-1-carboxylic acid tert-butyl ester, (7)

11-(2-Chloro-acetyl)-5,11-dihydro-benzo[e]pyrido[3,2-b][1,4]diazepin-6-one (144 mg) was stirred at 50° C. for 12 hrs in 2 ml dry DMF with 93 mg of N-tBOC-piperazine and 70 mg $K_2CO_3$. Reaction mixture was vacuum filtrated after cooling. Filtrate was evaporated in vacuo, and residue purified by flash chromatography using dichloromethane/methanol (97/3) as elution system.

1.3.6 Synthesis of 11-(2-Piperazin-1-yl-acetyl)-5,11-dihydro-benzor[e]pyrido-[3,2-b][1,4]diazepin-6-one dihydrochloride, (8)

4-[2-Oxo-2-(6-oxo-5,6-dihydro-benzo[e]pyrido[3,2-b][1,4]diazepin-11-yl)-ethyl]-piperazine-1-carboxylic acid tert-butyl ester (650 mg) was stirred at RT for 2 hrs in 15 ml dioxane and 1.5 ml conc. HCl. Reaction mixture was evaporated in vacuum and residue resuspended in 5 ml EtOH/10 ml toluene. Solvent was again removed in vacuo. Residue vas used without further purification. Yield 700 mg, mp 172-177° C.

1.3.7 Synthesis of 11-{2-[4-(tBoc-biocytinyl)-piperazin-1-yl]-acetyl}-5,11-dihydro-benzo[e]pyrido[3,2-b][1,4]diazepin-6-one, (9)

11-(2-Piperazin-1-yl-acetyl)-5,11-dihydro-benzo[e]pyrido[3,2-b][1,4]diazepin-6-one dihydrochloride (212 mg) was stirred at RT for 2 hrs in 10 ml methanol, 235 mg tBOC-Biocytin, 250 µl NMM and 165 mg DMT-MM. Reaction mixture was evaporated in vacuum and residue redissolved in 5% MeOH in dichloromethane. It was purified by flash chromatography using dichloromethane/methanol (95/5). Yield 430 mg.

1.3.8 Synthesis of 11-[2-(4-Biocytinyl-piperazin-1-yl)-acetyl]-5,11-dihydro-benzo[e]pyrido[3.2-b][1,4]diazepin-6-one, (10)

11-{2-[4-(tBoc-biocytinyl)-piperazin-1-yl]-acetyl}-5,11-dihydro-benzo[e]pyrido [3,2-b][1,4]diazepin-6-one (430 mg) was stirred at RT for 30 min in mixture of 3 ml dichloromethane and 3 ml TFA. Reaction mixture was evaporated in vacuum and residual TFA removed by azeotropic evaporation with mixture of EtOH/Toluene (1/2). Product was used without further purification.

1.3.9 Synthesis of thiocyanato 11-[2-(4-biocytinyl-piperazin-1-yl)-acetyl]-5,11-dihydro-benzo[e]pyrido[3,2-b][1,4]diazepin-6-one, (11)

11-[2-(4-Biocytinyl-piperazin-1-yl)-acetyl]-5,11-dihydro-benzo[e]pyrido-[3,2-b][1,4]diazepin-6-one (300 mg) was stirred at RT for 60 min., with 2 ml DMF, 300 ml NMM and 150 mg of DPT. Reaction mixture was evaporated in vacuum and residue triturated with 50 ml dry ether. The obtained product was redissolved in dichloromethane containing 5% isopropanole and was purified by flash chromatography over silica gel using dichloromethane/isopropanol (95/5).

1.4 Identification and Characterization of Second Binding Site of Pirenzepine The affinity reagent 11 was used to bind the target covalently from fractionations of crude cell extracts of D3 ES cells and other cell lines, subsequently the affinity purified material was analysed by 1D PAGE, immunostaining, and mass spectrometry.

1.4.1 Fractionation, Isolation, Western Blots, Mass Spectrometry

The subsequent fractionation, isolation and further analysis was performed according to published standard procedures (Sommer et al. 2004). A commercial anti-PARP antibody was used for staining Western blots. Mass spectrometry for independent identification of pirenzepine-tagged proteins was performed as described elsewhere recently (Vogt et al., 2003, Cahill et al., 2003).

Monoclonal anti-PARP antibody was purchased from BD BioScience (Cat# 556 362; clone C2-10). Secondary anti-mouse alkaline phosphatase conjugate was purchased from Sigma (Cat# A9316). NBT/BCIP-westernblot detection reagents came from Roche Diagnostics (Cat.# 1681451), Western Lightening CDP-Star chemiluminescence detection kit was supplied by Perkin Elmer (Cat.# NEL616001KT). For anti-PARP Western blotting experiments proteins were separated on 10% polyacryl amide gels and blotted onto nitrocellulose. Blots were blocked with 5% skimmed milk powder in Tris buffered saline containing 0,1% Tween-20 (TBS-T). Anti-PARP antibody was incubated over night at 4° C. using a 1:1000 dilution in milk powder TBS-T. Blots were subsequently washed 3 times using TBS-T. Second antibody was used at a dilution of 1:1000 for NBT/BCIP detection and 1:5000 for CDP-Star detection. Gels from various SIR2 containing fractions were blotted onto nitrocellulose membranes and visualized accordingly.

For SIR-2 staining the following antibodies were used: primary Ab: A-SiR 2 (Upstate, biomol 07-131; Lot:22073); 1:5000 in 5% BSA/1×TBST; secondary Ab: A-Rabbit PE(A-0545) 1:1000 in 5% BSA/1×TBST: Cox-2 staining was obtained accordingly by using an antibody from Alexis, (ALX-210-711-1) anti-COX-2 (Cyclooxygenase-2); Rabbit, polyclonal; 1:1000 dilution; secondary antibody was anti-rabbit-AP (Sigma, A3937, 1:1000)

iNOS staining was performed using a polyclonal anti-iNOS, Alexis, 1:1000). Blots were washed in TBS/1.0% Tween and incubated with the appropriate secondary antibody-horseradish peroxidase conjugate (anti-rabbit IgG, Sigma, 1:2000).

1.4.2 PARP Inhibition Test

A PARP inhibition assay from R&D Systems was used (Cat.No. TA4669) according to instructions of the supplier.

1.4.3 SIR2 Activity Assay

For measurements of SIR2 activities, the quantitative test kit for NAD-dependent histone deacetylase activity CycLex® SIR2 Assay kit (Cat# CY-1151) was used according to instructions of manufacturer (CycLex Co., Ltd. 1063-103 Ohara, Tera-Sawaoka Ina, Nagano 396-0002 Japan). All substances tested in the SIR assay were cross-checked for their influence on the lysyl-endopeptidase. For this control an already deacetylated substrate peptide was used in order to measure directly lysyl-endopeptidase activity.

1.4.4 Experimental Model for Inflammation in Neuronal and Non-Neuronal Cells LPS challenge of 3T3 fibroblasts, A 549 cells, V56 embryonic stem cells and neurally differentiated V56 embryonic stem cells was equally performed by exposing cells to 100 ng/ml lipopolysaccharide (LPS, E.coli 0111:B4 LPS from Sigma) for 60 min in the presence or absence of pirenzepine and related compounds. Cell pellets were further investigated by Western blot staining with anti Cox-2 and anti iNOS antibodies of 1D polyacrylamide gels.

2. Results

2.1 Neuroprotective Effect of Pirenzepine in Chemical Ischemia

FIG. 2 shows the neuroprotective effects of pirenzepine and LS-75 in the functional models outlined in the methods section.

Whereas control cells had a survival rate of 4.8±3.4% (number of cells at first stimulation: 189 and number of cells at second stimulation after chemical ischemia, pirenzepine-treated cells had a survival rate of 72.1±4.4% (number of cells at first stimulation: 68 and number of cells at second stimulation after chemical ischemia: 49) (FIG. 2b). In the lower part (FIG. 2f) a summary is given for neuroprotective effects of Pirenzepine and LS-75 in three different functional models: induction of chemical ischemia as described, induction of excitotoxic cell death by 100 µM NMDA (or 100 µM HCA as in Sommer et al. 2004) and induction of neuronal death by 10 µM β-amyloid 1-40 (Bachem, Germany); All three challenges induce an initial calcium overload, which obviously initiates proapoptotic and proinflammatory events, leading eventually to neuronal dysfunction and cell death. This is shown in FIG. 2c, by Western blots of cellular fractions with or without Pirenzepine/LS-75 application, stained for apoptotic markers PARP-1 and inflammatiory marker Cox-2. Additional information on statistics of these experiments are provided in FIGS. 2d and 2e.

2.2 Identification of PARP as a Target of Pirenzipine

We then proceeded to synthesize reactive pirenzepine derivatives as shown in FIG. 1; Pirenzepine was used as a starting structure for the synthesis of an irreversible, i.e. covalently attached, affinity reagent for target proteins. A reactive —SCN group binds to lysins in or near the binding site of the compound. A biotinylated linker serves for enrichment of bound protein. The final affinity reagent, thiocyanato-11-[2-(4-biocytinyl-piperazin-1-yl)-acetyl]-5,11-dihydro-benzo[e]pyrido [3,2-b] [1,4] diazepin-6-one (compound (11), FIG. 1), was used to bind the target covalently from fractionations of crude cell extracts of D3 embryonic stem cells, subsequently the affinity purified material was analysed by 1D PAGE (FIG. 3a), mass spectrometry and immunostaining. MALDI-TOF analysis of the silver stained gels indicated the presence of PARP-1 and SIR-2 in enriched fractions, which was confirmed independently by corresponding staining of Western blots of 1D gels with a monoclonal anti-PARP antibody (bands at 113 and 89 kD, FIG. 3b) and a specific antibody against SIR-2 (110 kD, FIG. 3c).

In the affinity tag incubation 0.5 ml NP 40 stem cell extract (2.3 mg protein) was incubated with 1 µM affinity tag for 60 min at 37° C. A surplus of affinity tag was removed by NAP10 gel filtration. The reaction mixture was bound to streptavidin agarose. Elution occurred with elution buffer (2% SDS, 62.5 mM Tris-pH 6.8) for 10 min at room temperature and 10 min at 95° C. For binding to PARP, a mouse monoclonal antibody (BD Biosciences 1:2000) was used. As detection antibody, an anti-mouse alkaline phosphatase antibody conjugate (1:1000 and NBT/BCIP substrate) was used.

2.3 PARP Inhibition Test

Enzymatic tests for SIR-2 and PARP-1 activities, shown in FIG. 4a reveal, that although the affinity tag interacts with both proteins, pirenzepine and LS-75 are PARP-1 inhibitors with IC50-values of 200 and 18 µM, respectively and as well appear to be inhibiting SIR-2, but only at very high concentrations, with IC50-values beyond 1-5 mM. The table in FIG. 4 includes controls: nicotine amide had an IC50-value for SIR-2 inhibition of approx. 55 µM in our assay, and a typical PARP-1 inhibitor like phenanthridone had an IC50-value of 7 µM in our assay, which is in agreement with previous reports (North, B.J., Verdin, E. Sirtuins: SIR2-related NAD-dependent protein deacetylases. *Genome Biol.* 5, 224f, 2004; Southan G J, Szabo C. Poly(ADP-ribose) polymerase inhibitors. Curr Med Chem. 2003 February;10(4):321-40).

Further examples of preferred structurally related compounds suitable for the present invention are:
- 6H-pyrido[2,3-b][1,4]benzodiazepin-6-one (PBD or LS-75), (core structure, used in PARP1 inhibition test and cell based neuroprotection assay),
- Danfenacin hydrobromide (Enablex™, Novartis, M3 muscarinic antagonists, on market in 2004),
- Alvameline tartrate (Lu 25-109T, Lundbeck, M1 agonist, M2 & M3 antagonist, disconnected in Phase III of clinical studies since not efficient in treatment of AD)
- Impatropium (M1, M2 and M3 antagonist, bronchodilatator)
- Tiotropium bromide (Spiriva, Boehringer, M1, M2 and M3 antagonist, bronchodilatator, on the market since 2001-2).
- Metoclopramide, muscarinic antagonist (nonselective one), dopamine D2 antagonist
- Telenzepine Dihydrochloride, Sigma,
- Clozepine,
- Viramune,
- Pipenzolate, by Sigma
- QNB, by Sigma

2.4. General Cytoprotective Effects After an Inflammatory Challenge (LPS Exposure)

We stimulated 3T3 fibroblasts (FIG. 5a), A549 cells (FIG. 5b), undifferentiated V56 embryonic stem cells (FIG. 5c) and neurally differentiated V56 embryonic stem cells (FIG. 5d with 100 ng/ml lipopolysaccharide (*E.coli* 0111: B4 LPS from Sigma) for 60 min. As an inflammatory marker we again quantified expression of Cox-2 and iNOS by appropriate antibody staining of Western blots of 1D PA gels. The results show that Pirenzepine and related substances like LS-75 protect cells from LPS-induced death (FIG. 5a-d), and ii) that this protective effect is accompanied by a decreased expression of inducible inflammatory markers iNOS and Cox-2 (similar to FIG. 2, not shown). Cell survival was assessed by Trypan Blue staining.

2.5. Influence/Dependence of Effects of Pirenzepine and Related Substances Upon Assembly of Cholesterol-Rich Rembrane Domains Next to the direct effect on PARP-1 and SIR-2 the substances appear to bring about their effects via transient membrane domains, cholesterol-rich lipid rafts, which are thought to be an important in a variety of related signalling pathways (Cuschieri J. Implications of lipid raft disintegration: enhanced anti-inflammatory macrophage phenotype. Surgery. 2004 August;136 (2):169-75.; Chu C L, Buczek-Thomas J A, Nugent M A. Heparan sulphate proteoglycans modulate fibroblast growth factor-2 binding through a lipid raft-mediated mechanism. Biochem J. 2004 Apr. 15;379(Pt 2):331-41; Argyris E G, Acheampong E, Nunnari G, Mukhtar M, Williams K J, Pomerantz R J.Human immunodeficiency virus type 1 enters primary human brain microvascular endothelial cells by a mechanism involving cell surface proteoglycans independent of lipid rafts. J Virol. 2003 November;77 (22):12140-51; Nagy P, Vereb G, Sebestyen Z, Horvath G, Lockett S J, Damjanovich S, Park J W, Jovin T M, Szollosi J. Lipid rafts and the local density of ErbB proteins influence the biological role of homo- and heteroassociations of ErbB2. J Cell Sci. 2002 Nov. 15;115(Pt 22):4251-62).

In FIG. 6 we show that the neuroprotective effect of Pirenzepine and related substances like PBD/LS-75 does not occur in the presence of "raft"-disrupting conditions (FIG. 6a; β-methyl-cyclodextrin or filipin) and we conclude, that Pirenzepine and related substances like PBD/LS-75 during do require, at least to some extent, the presence of cholesterol-rich membrane rafts.

2.6 PARP Inhibition Under Cellular Conditions

A semiquantitative assay for determining PARP inhibition under cellular conditions using a specific antibody against poly-ADP-ribosylated proteins (primary antibody: anti-poly-(ADP-ribose)-antigen; mouse, Biomol; Cat # SA-216; secondary antibody: anti-mouse, AP; Sigma A9316) was performed. As can be seen in FIG. 8, the ischemic insult of neural cells by KCN/glucose deprivation (described elswhere in Methods section), induces a substantial increase in of staining with this antibody, in particular of a host of proteins in the 100-250 kD range. This effect is reversed by addition of neuroprotective concentrations of LS-75; here we show the decrease of poly-ADP-ribosylated proteins during ischemic insult by the presence of 1 and 10 µM LS-75, respectively. The IC 50 of these effects lies below 1 µM (approx. 0.3 µM).

Taken together, in the R & D assay, a histone mix and biotinylated NAD and a recombinant monomeric PARP-1 are used; the IC 50 is ~20 µM. Under cellular conditions PARP-1 poly-ADP-ribosylates a host of nuclear proteins, including topoisomerase 1, 14-3-3 g and PARP-1 itself. Thus under cellular conditions, the self-modification of PARP-1 and dimerization are regulating its activity, moreover there is a tight interplay with PARG (poly-ADP- ribosyl-glycohydroxylase).

The quantification of poly-ADP-ribosylated proteins by appropriate Western blots exactly matches dose-reponse relationship and time frames of the in vitro neuroprotection; we thus conclude that the conditions of the R&D assay only partially reflect cellular conditions of PARP-1 activity.

2.7 Blood-Brain-Barrier Passage of Pirenzepine and Related Compounds

The blood brain barrier (BBB) passage of Pirenzepine and its metabolite LS-75 was determined. As already shown in FIG. 6, the neuroprotective effects of e.g. LS-75 during ischemia appears to be dependent on the presence of (lipid raft-forming) cholesterol, because the cholesterol-depleting agent methyl-b-cyclodextrin prevents neuroprotection. This is in line with the idea that these rafts play a crucial role in underlying signal transduction (see also FIG. 7). As shown in FIG. 9, we used standard HPLC detection (according to Dusci et al., (2002) J. Chromatogr. B, 773, 191 ff. and Huq et al., (2003) Simplified method development for the extraction of acidic, basic and neutral drugs with a single SPE sorbent-strata X; Phenomenex Inc. Torrance, Calif., USA; Application note SPE/TN-004) to quantify Pirenzepine and its two major metabolites (dm-Pirenzepine and LS-75) in serum and cerebrospinal fluid (CSF) of test animals. For these experiments, sets of each 32 rats were given 50 mg/kg Pirenzepine or LS-75 and either killed after 3 h or 6 h, then their plasma and CSF were collected (128 animals); literature for available information about pharmacokinetics and bioavailability of Pirenzepine, underlying the rationale of these experiments is e.g.: Jaup and Blomstrand, 1980, Scand. J. Gastroenterol. 66, 35ff.; Homon et al., 1987, Therapeutic Drug Monitoring 9, 236ff.).

Our results show peak concentrations of Pirenzepine and dm-Pirenzepine in plasma of about 2-3 h; in the rat there appears to be virtually no passage of these two substances into the brain (FIG. 10). In one further set of animal experiments we pretreated an identical set of test rats with Mevastatin, an antibiotic which acts as a potent inhibitor of 3-hydroxy-3-methylglutaryl coenzyme A reductase, the rate-limiting enzyme in cholesterol biosynthesis at a concentration of 0.15 mg/day for 14 days, prior to oral gavage of 50 mg Pirenzepine and LS-75. We found about 50% higher concentrations of Pirenzepine, dm-Pirenzepine and LS-75 in plasma, but far less LS-75 in CSF (data not shown). This is an indication that Pirenzepine partitions into cholesterol-rich parts of membranes, which might also be associated with the BBB-passage of LS-75.

2.8 Neuroprotective Effect in Vitro

When LS-75 is applied directly there is a substantial passage through the BBB as shown in FIG. 11; the crucial point is that even after Pirenzepine application, but with longer peak times, we observe increasing amounts of the metabolite LS-75 in the brain. In other words, Pirenzepine serves as a vehicle to transport LS-75, the more active PARP-1 inhibitor into the brain; this is an absolutely novel principle: potentially the muscarinic binding site of Pirenzepine just serves to target the whole molecule (which is not very anti-PARP-1 active in the periphery) to cholesterol-rich rafts and subsequently deliver an active part of the molecule (in this case the metabolite and PARP-1 inhibitor LS-75) into the brain. We claim dual mode of related substances, with one moiety binding to cholesterol-rich rafts or to a raft protein (here a muscarinic receptor), and subsequently enabling passage of BBB for an active portion of the whole molecule, in this case enriching a PARP-1 inhibitor (LS-75) in the brain.

In an in vivo experiment, related to traumatic brain injury (TBI), we could show a neuroprotective effect for neurons of the contralateral side to trauma. In TBI, very often secondary neurodegeneration contralateral to the side of injury occurs, probably due to calcium/glutamate driven proapoptotic mechanisms.

The model employed a direct shock to the dura via a burrhole, animals were treated according to the following schemes: Vehicle, LS-75, 8 animals per group starting the study, 2 spare animals; animals were sacrificed 44 h after injury, the endpoints were survival, post injury signs, lesion size by FLB (Fast Luxol Blue) and EMAP (Endothelial, Monocyte, Activating Peptide) staining. The dosing i.p. 100 mg/kg 2 h prior to injury; 40 mg/kg i.p. 2 h after injury; 40 mg/kg i.p. 8 h after injury; 40 mg/kg i.p. 17 h after injury; 40 mg/kg i.p. 25 h after injury; 70 mg/kg i.p. 34 h after injury; Formulation: LS-75 was prepared as a DMSO slurry (not solution) in a mortar and pestle and saline will be added slowly with grinding to reach 4% DMSO final concentration. The suspension is maintained at room temperature and the preparation used for the duration of the study. To vary dose, the volume injected may change. Volume for 100 mg/kg was be 4 mL/kg.

In FIGS. 12 and 13 the corresponding results are shown. 44 h after induction of traumatic brain injury (TBI) in an experimental animal model, the secondary lesions were reduced by approx. 50% in LS-75 treated animals as compared to vehicle controls. EMAP produced clear labelling of cells at 44 h. EMAP labels were largely associated with the immediate zone of injury. An analysis was carried out by a "blinded" neurophysiologist who remarked as follows: "EMAP staining in one group appears to be restricted to the lesion, whereas in another group, it is more diffuse and associated with vessels". The diffuse staining was seen in the vehicle group.

The morphological stains HE and Luxol Fast Blue were both useful in displaying alterations in cells in the contralateral hemisphere. Luxol Fast Blue, however, produced a more readily observed staining and so focussed on it here. An increase in staining by LFB indicates that a cell is in transformation and probably reflects the mobilization of phospholipids and thus neuronal damage.

2.9 Conclusions

Our results clearly show, that pirenzepine and related compounds, in particular PBD/LS-75 bind to PARP and act as PARP inhibitors.

This property of pirenzepine and related compounds like LS-75 was previously unknown and allows the conclusion that pirenzepine and related compounds may be used as cytoprotective agents for medical applications. Due to the dual mode of action (M1 muscarinic receptor) inhibition and PARP inhibition) these compounds may have superior properties over pure PARP inhibitors.

The cytoprotective properties of these and other related compounds are rather due to a hitherto unknown dual mode of action namely muscarinic/PARP. This novel mixed type of activity can be used for new high throughput screening of existing chemical libraries for identification of novel cytoprotective agents for the treatment of various indications as outlined above.

Generally the invention relates to cytoprotective properties of compounds with a dual M1/PARP1 modulating activity for the prevention or treatment of neurological disorders.

Example 2

SIR2 Inhibition or Interaction

1. Materials and Methods 1.1 SIR2 Activity Test

For measurements of SIR2 activities, the quantitative test kit for NAD-dependent histone deacetylase activity CycLex® SIR2 Assay kit (Cat# CY-1151) was used according to instructions of manufacturer (CycLex Co., Ltd. 1063-103 Ohara, Tera-Sawaoka Ina, Nagano 396-0002 Japan).

1.2 Western Blot

Gels from various SIR2 containing fractions were blotted onto nitrocellulose membranes according to standard procedures. Proteins were visualized using enhanced chemoluminescence (ECL), for Sir 2 staining the following antibodies were used: primary Ab: A-SiR 2 (Upstate, biomol 07-131; Lot:22073); 1:5000 in 5% BSAr/1×TBST; secondary Ab: A-Rabbit PE (A-0545) 1:1000 in 5% BSA/1×TBST.

2. Results 2.1 SIR2 Interaction With Pirenzepine Affinity Tag, Identification of SIR2 as a Target of Pirenzipine FIG. 3c shows that the pirenzepine-affinity tag prepared according to Example 1 irreversibly binds to SIR2 and provides enrichment of this additional target, as demonstrated by immunostaining 1D gels of extracts of V56 cells with a specific antibody. Details are provided in the legend to FIG. 3.

2.2 SIR2 Activity Test

Using a raw extract from murine embryonic stem cells as described in Sommer et al., (2004) and the commercially available SIR2 activity test described, the following values were recorded in comparison to raw extracts not treated with the drugs.

In FIG. 4 results of a SIR-2 activity test are shown. Pirenzepine and PBD/LS-75 obviously bind to SIR-2 and have a weak inhibitory effect. This opens the route to a corresponding screening for novel structure/activity relationship studies of related compounds.

2.3 Conclusions

Our results clearly show, that pirenzepine and related structures bind to SIR-2 and can act as weak SIR-2 inhibitors.

This property of pirenzepine and related compounds was previously unknown. Due to this mode of action, these compounds may be used as cytoprotective agents and may have superior properties over pure PARP inhibitors.

Thus, the invention also generally relates to cytoprotective properties with combined M1/PARP1/SIR-2 modulating activity. Moreover the substances appear to mediate their effects via cholesterol-rich membrane domains, called lipid rafts, as shown in FIG. 6, they thus generally act via or target a special assembly of proteins associated with these lipid rafts, like neuregulin, heparanesulfate binding proteins, NMDA receptors, nicotinic receptors, $GABA_A$ receptors ErbB receptors and others. A summary of lipid raft assembly is given in FIG. 7.

Example 3

Cox-2 and iNOS Expression in LPS Challenge and Chemical Ischemia of Neuronal and Non-Neuronal Cells In the various cellular insult models described here, we always observe an initial calcium overload of cells, which subsequently leads to apoptotic cell death, concomitant with increase of apoptotic and proinflammatory markers such as Cox-2 (see FIG. 2c and corresponding results for LPS experiments).

Conclusion

The neuro- and more generally cytoprotective effects of Pirenzepine and related compounds like PBD/LS-75 on the one hand appear to be mediated via PARP-1 and SIR-2 binding and inhibition, and on the other hand appear to require a special assembly of membrane associated protein complexes in so-called lipid rafts.

A common feature of all the different cellular challenges applied here in the context of said substances is an initial cytotoxic calcium overload, which subsequently proceeds to inflammatory and apoptotic events as demonstrated by PARP-1/iNOS/cox-2 staining. Thus the invention encompasses the use of these substances as treatment in all disease indications where calcium overload and inflammatory/apoptotic events are thought to play a major role or potentially are crucial. This includes neurological disorders and inflammatory conditions associated with neurological disorders, particularly Alzheimer's and Parkinson's disease, traumatic brain injury, ALS, multiple sclerosis, migraine and chronic pain syndromes and other diseases as mentioned above.

Thus, the invention generally relates to cytoprotective properties with combined M1/PARP1/SIR2 modulating activity.

FURTHER REFERENCES

1. Cahill M A, Wozny W, Schwall G, Schroer K, Holzer K, Poznanovic S, Hunzinger C, Vogt J A, Stegmann W, Matthies H, Schrattenholz A. (2003). Analysis of relative isotopologue abundances for quantitative profiling of complex protein mixtures labelled with the acrylamide/D3-acrylamide alkylation tag system. Rapid Communications in Mass Spectrometry, 2003, 17:1283-1290.
2. Sommer S, Hunzinger C, Schillo S, Klemm M, Biefang-Arndt K, Schwall G, Pütter S, Hoeizer K, Schroer K, Stegmann W Schrattenholz A (2004) Molecular analysis of homocysteic acid-induced neuronal stress. Journal of Proteome Research 3, (3), 572-581.
3. Okabe S, Forsberg-Nilsson K, Spiro A C, Segal M, McKay R D G (1996), Development of neuronal precursor cells and functional postmitotic neurons from embryonic stem cells in vitro. Mech Dev. 59: 89-102.
4. Kume T, Nishikawa H, Taguchi R, Hashino A, Katsuki H, Kaneko S, Minami M, Satoh M, Akaike A. (2002) Antagonism of NMDA receptors by sigma receptor ligands attenuates chemical ischemia-induced neuronal death in vitro. Eur J Pharmacol. 455:91-100.
5. Shevchenko A, Wilm M, Vorm O, Mann M.(1996). Mass spectrometric sequencing of proteins silver-stained polyacrylamide gels. Analytical Chemistry. 1996; 68:850-858.
6. Vogt J A, Schroer K, Holzer K, Hunzinger C, Klemm M, Biefang-Arndt K, Schillo S, Cahill M A, Schrattenholz A, Matthies H, Stegmann W. (2003). Protein abundance quantification in embryonic stem cells using incomplete metabolic labelling with 15N amino acids, matrix-assisted laser desorption/ionisation time-of-flight mass spectrometry, and analysis of relative isotopologue abundances of peptides. Rapid Commun Mass Spectrom. 2003;17:1273-1282
7. Vuong G L, Weiss S M, Kammer W, Priemer M, Vingron M, Nordheim A, Cahill MA, (2000) Improved sensitivity proteomics by postharvest alkylation and radioactive labelling of proteins. Electrophoresis, 2000; 21: 2594-2605.
8. Bakondi E, Bai P, Erdelyi K, Szabo C, Gergely P, Virag L. Cytoprotective effect of gallotannin in oxidatively stressed HaCaT keratinocytes: the role of poly(ADP-ribose) metabolism. Exp Dermatol. 2004 March;13(3):170-8.
9. Bai P, Bakondi E, Szabo E, Gergely P, Szabo C, Virag L. Partial protection by poly(ADP-ribose) polymerase inhibitors from nitroxyl-induced cytotoxicity in thymocytes. Free Radic Biol Med. 2001 Dec. 15;31 (12):1616-23.
10. Virag L, Szabo C. Purines inhibit poly(ADP-ribose) polymerase activation and modulate oxidant-induced cell death. FASEB J. 2001 January;15(1):99-107.

The invention claimed is:

1. A method for the treatment of neurodegenerative or neuroinflammatory conditions in disorders such as dementia, Parkinson's disease, Alzheimer's disease, stroke, or schizophrenia in a patient in need of such treatment comprising administering to the patient an effective amount of pirenzepine, LS-75, or a salt thereof.

2. The method of claim 1, wherein said effective amount of a compound of pirenzepine, LS-75, or a salt thereof is administered to the patient without other medicaments.

3. The method of claim 1, wherein said patient suffers from neurodegenerative or neuroinflammatory conditions wherein the disorder is dementia.

4. The method of claim 1, wherein said patient suffers from Parkinson's disease.

5. The method of claim 1, wherein said patient suffers from Alzheimer's disease.

6. The method of claim 1, wherein said patient has suffered a stroke.

7. The method of claim 1, wherein said patient suffers from schizophrenia.

* * * * *